(12) United States Patent
Bandhauer et al.

(10) Patent No.: US 7,984,990 B2
(45) Date of Patent: *Jul. 26, 2011

(54) OPHTHALMIC LENS WITH MULTIPLE PHASE PLATES

(75) Inventors: Mark H Bandhauer, Orange, CA (US);
Alan J Lang, Long Beach, CA (US)

(73) Assignee: Abbot Medical Optics Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/566,348

(22) Filed: Sep. 24, 2009

(65) Prior Publication Data

US 2010/0014049 A1      Jan. 21, 2010

Related U.S. Application Data

(63) Continuation of application No. 12/323,126, filed on Nov. 25, 2008, now Pat. No. 7,922,326, which is a continuation of application No. 11/259,534, filed on Oct. 25, 2005, now Pat. No. 7,455,404.

(51) Int. Cl.
| | |
|---|---|
| *G02C 7/06* | (2006.01) |
| *G02C 7/04* | (2006.01) |
| *G02B 27/44* | (2006.01) |
| *A61F 2/16* | (2006.01) |

(52) U.S. Cl. ........ 351/168; 351/161; 351/171; 351/172; 359/565; 359/571; 623/6.3

(58) Field of Classification Search ........... 351/168, 351/171, 172, 161; 359/565, 571; 623/6.3, 623/6.31

See application file for complete search history.

(56) References Cited

U.S. PATENT DOCUMENTS

| | | | |
|---|---|---|---|
| 3,722,986 | A | 3/1973 | Tagnon |
| 4,340,283 | A | 7/1982 | Cohen |

(Continued)

FOREIGN PATENT DOCUMENTS

EP            37529 A1      10/1981

(Continued)

OTHER PUBLICATIONS

"Optical Design," Military Standardization Handbook, 1962, Chapter 4, U.S. Department of Defense MIL-HDBK-141, 4-1-4-19.

(Continued)

*Primary Examiner* — Scott J Sugarman
(74) *Attorney, Agent, or Firm* — Abbott Medical Optics Inc.

(57) ABSTRACT

An ophthalmic lens for providing a plurality of foci includes an optic having an anterior surface, a posterior surface, and an optical axis. The ophthalmic lens has a first region and a second region. The first region has a first refractive optical power and includes a first base curvature having a finite first radius of curvature and a first phase plate having at least one diffraction order with a diffractive optical power. The first region is configured for forming a first focus and a second focus. The second region has a second refractive optical power and includes a second base curvature having a finite second radius of curvature that is different from the first radius of curvature and a second phase plate having at least one diffraction order with a diffractive optical power. The second region is configured for forming a third focus that is between the first focus and the second focus. The ophthalmic lens may be configured so the first focus provides distant vision, the second focus provides near vision, and the third focus provides intermediate vision.

11 Claims, 9 Drawing Sheets

U.S. PATENT DOCUMENTS

| | | |
|---|---|---|
| 4,460,275 A | 7/1984 | Spriggs |
| 4,504,892 A | 3/1985 | Zulfilar |
| 4,504,982 A | 3/1985 | Burk |
| 4,580,883 A | 4/1986 | Shinohara |
| 4,606,626 A | 8/1986 | Shinohara |
| 4,637,697 A | 1/1987 | Freeman |
| 4,640,593 A | 2/1987 | Shinohara |
| 4,641,934 A | 2/1987 | Freeman |
| 4,642,112 A | 2/1987 | Freeman |
| 4,655,565 A | 4/1987 | Freeman |
| 4,710,193 A | 12/1987 | Volk |
| 4,762,408 A | 8/1988 | Shinohara |
| 4,856,889 A | 8/1989 | Guilino et al. |
| 4,881,804 A | 11/1989 | Cohen |
| 4,881,805 A | 11/1989 | Cohen |
| 4,898,461 A | 2/1990 | Portney |
| 4,936,666 A | 6/1990 | Futhey |
| 4,957,506 A | 9/1990 | Mercier |
| 4,978,211 A | 12/1990 | Cornu et al. |
| 4,995,714 A | 2/1991 | Cohen |
| 4,995,715 A | 2/1991 | Cohen |
| 5,017,000 A | 5/1991 | Cohen |
| 5,019,098 A | 5/1991 | Mercier |
| 5,050,981 A | 9/1991 | Roffman |
| 5,054,905 A | 10/1991 | Cohen |
| 5,056,908 A | 10/1991 | Cohen |
| 5,061,058 A | 10/1991 | Guilino et al. |
| 5,076,684 A | 12/1991 | Simpson et al. |
| 5,089,023 A | 2/1992 | Swanson |
| 5,089,024 A | 2/1992 | Christie et al. |
| 5,096,285 A | 3/1992 | Silberman |
| 5,100,226 A | 3/1992 | Freeman |
| 5,104,212 A | 4/1992 | Taboury et al. |
| 5,112,351 A | 5/1992 | Christie et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,148,205 A | 9/1992 | Guilino et al. |
| 5,173,723 A | 12/1992 | Volk |
| 5,178,636 A | 1/1993 | Silberman |
| 5,191,366 A | 3/1993 | Kashiwagi |
| 5,220,359 A | 6/1993 | Roffman |
| 5,225,858 A | 7/1993 | Portney |
| 5,229,797 A | 7/1993 | Futhey et al. |
| 5,236,970 A | 8/1993 | Christ et al. |
| 5,257,132 A | 10/1993 | Ceglio et al. |
| 5,344,447 A | 9/1994 | Swanson |
| 5,349,394 A | 9/1994 | Freeman et al. |
| 5,349,471 A | 9/1994 | Morris et al. |
| 5,384,606 A | 1/1995 | Koch et al. |
| 5,408,281 A | 4/1995 | Zhang |
| 5,444,106 A | 8/1995 | Zhou et al. |
| 5,446,508 A | 8/1995 | Kitchen |
| 5,448,312 A | 9/1995 | Roffman et al. |
| 5,485,228 A | 1/1996 | Roffman et al. |
| 5,581,405 A | 12/1996 | Meyers et al. |
| 5,589,982 A | 12/1996 | Faklis et al. |
| 5,629,800 A | 5/1997 | Hamblen |
| 5,652,638 A | 7/1997 | Roffman et al. |
| 5,674,284 A | 10/1997 | Chang et al. |
| 5,682,223 A | 10/1997 | Menezes et al. |
| 5,683,457 A | 11/1997 | Gupta et al. |
| 5,684,560 A | 11/1997 | Roffman et al. |
| 5,699,142 A | 12/1997 | Lee et al. |
| 5,715,031 A | 2/1998 | Roffman et al. |
| 5,715,091 A | 2/1998 | Meyers |
| 5,724,258 A | 3/1998 | Roffman |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,800,532 A | 9/1998 | Lieberman |
| 5,805,260 A | 9/1998 | Roffman et al. |
| 5,822,091 A | 10/1998 | Baker |
| 5,838,496 A | 11/1998 | Maruyama et al. |
| 5,847,802 A | 12/1998 | Menezes et al. |
| 5,888,122 A | 3/1999 | Gupta et al. |
| 5,895,422 A | 4/1999 | Hauber |
| 5,895,610 A | 4/1999 | Chang et al. |
| 5,929,969 A | 7/1999 | Roffman |
| 5,968,095 A | 10/1999 | Norrby |
| 6,007,747 A | 12/1999 | Blake et al. |
| 6,019,472 A | 2/2000 | Koester et al. |
| 6,050,687 A | 4/2000 | Bille et al. |
| 6,070,980 A | 6/2000 | Obara et al. |
| 6,082,856 A | 7/2000 | Dunn et al. |
| 6,086,204 A | 7/2000 | Magnante |
| 6,089,711 A | 7/2000 | Blankenbecler et al. |
| 6,095,651 A | 8/2000 | Williams et al. |
| 6,120,148 A | 9/2000 | Fiala et al. |
| 6,139,145 A | 10/2000 | Israel |
| 6,145,987 A | 11/2000 | Baude et al. |
| 6,154,323 A | 11/2000 | Kamo |
| 6,199,986 B1 | 3/2001 | Williams et al. |
| 6,215,096 B1 | 4/2001 | Von Wallfeld et al. |
| 6,224,211 B1 | 5/2001 | Gordon |
| 6,231,603 B1 | 5/2001 | Lang et al. |
| 6,270,220 B1 | 8/2001 | Keren |
| 6,325,510 B1 | 12/2001 | Golub et al. |
| 6,338,559 B1 | 1/2002 | Williams et al. |
| 6,353,503 B1 | 3/2002 | Spitzer et al. |
| 6,413,276 B1 | 7/2002 | Werblin |
| 6,429,972 B1 | 8/2002 | Ota et al. |
| 6,439,720 B1 | 8/2002 | Graves et al. |
| 6,457,826 B1 | 10/2002 | Lett |
| 6,474,814 B1 | 11/2002 | Griffin |
| 6,497,483 B2 | 12/2002 | Frey et al. |
| 6,511,180 B2 | 1/2003 | Guirao et al. |
| 6,520,638 B1 | 2/2003 | Roffman et al. |
| 6,536,899 B1 | 3/2003 | Fiala |
| 6,547,391 B2 | 4/2003 | Ross, III et al. |
| 6,554,425 B1 | 4/2003 | Roffman et al. |
| 6,554,859 B1 | 4/2003 | Lang et al. |
| 6,576,012 B2 | 6/2003 | Lang |
| 6,582,076 B1 | 6/2003 | Roffman et al. |
| 6,585,375 B2 | 7/2003 | Donitzky et al. |
| 6,609,673 B1 | 8/2003 | Johnson |
| 6,609,793 B2 | 8/2003 | Norrby et al. |
| 6,616,275 B1 | 9/2003 | Dick et al. |
| 6,685,315 B1 | 2/2004 | De Carle |
| 6,709,103 B1 | 3/2004 | Roffman et al. |
| 6,755,524 B2 | 6/2004 | Rubinstein et al. |
| 6,791,754 B2 | 9/2004 | Ogawa |
| 6,802,605 B2 | 10/2004 | Cox et al. |
| 6,818,158 B2 | 11/2004 | Pham et al. |
| 6,827,444 B2 | 12/2004 | Williams et al. |
| 6,830,332 B2 | 12/2004 | Piers et al. |
| 6,835,204 B1 | 12/2004 | Stork et al. |
| 6,848,790 B1 | 2/2005 | Dick et al. |
| 6,851,803 B2 | 2/2005 | Wooley et al. |
| 6,884,261 B2 | 4/2005 | Zadno-Azizi et al. |
| 6,957,891 B2 | 10/2005 | Fiala |
| 6,972,032 B2 | 12/2005 | Aharoni et al. |
| 7,048,759 B2 | 5/2006 | Bogaert et al. |
| 7,111,938 B2 | 9/2006 | Andino et al. |
| 7,188,949 B2 * | 3/2007 | Bandhauer et al. .......... 351/168 |
| 7,198,640 B2 | 4/2007 | Nguyen |
| 7,377,640 B2 | 5/2008 | Piers et al. |
| 7,377,641 B2 | 5/2008 | Piers et al. |
| 7,455,404 B2 * | 11/2008 | Bandhauer et al. .......... 351/168 |
| 7,543,937 B2 | 6/2009 | Piers et al. |
| 2002/0093701 A1 | 7/2002 | Zhang et al. |
| 2002/0105617 A1 | 8/2002 | Norrby et al. |
| 2002/0122153 A1 | 9/2002 | Piers et al. |
| 2003/0014107 A1 | 1/2003 | Reynard |
| 2003/0063254 A1 | 4/2003 | Piers et al. |
| 2003/0169491 A1 | 9/2003 | Bender et al. |
| 2004/0080710 A1 | 4/2004 | Wooley et al. |
| 2004/0088050 A1 | 5/2004 | Norrby et al. |
| 2004/0138746 A1 | 7/2004 | Aharoni et al. |
| 2004/0156014 A1 | 8/2004 | Piers et al. |
| 2004/0169820 A1 | 9/2004 | Dai et al. |

| | | | |
|---|---|---|---|
| 2004/0246440 | A1 | 12/2004 | Andino et al. |
| 2004/0252274 | A1 | 12/2004 | Morris et al. |
| 2005/0057720 | A1 | 3/2005 | Morris et al. |
| 2005/0099589 | A1 | 5/2005 | Ishak |
| 2005/0264757 | A1 | 12/2005 | Morris et al. |
| 2006/0004446 | A1 | 1/2006 | Aharoni et al. |
| 2006/0139570 | A1 | 6/2006 | Blum et al. |
| 2007/0002444 | A1 | 1/2007 | Piers et al. |

FOREIGN PATENT DOCUMENTS

| | | |
|---|---|---|
| EP | 335731 A2 | 10/1989 |
| EP | 342895 A2 | 11/1989 |
| EP | 355230 A2 | 2/1990 |
| EP | 375291 A2 | 6/1990 |
| EP | 412751 A2 | 2/1991 |
| EP | 457553 A2 | 11/1991 |
| EP | 470811 A2 | 2/1992 |
| EP | 605841 A1 | 7/1994 |
| EP | 681198 A1 | 11/1995 |
| EP | 1376203 A2 | 1/2004 |
| JP | 3011315 A2 | 1/1991 |
| WO | WO-9222264 A1 | 12/1992 |
| WO | WO-9413225 A1 | 6/1994 |
| WO | WO-9724639 A1 | 7/1997 |
| WO | WO-9831299 A2 | 7/1998 |
| WO | WO-9907309 A1 | 2/1999 |
| WO | WO-9923526 A1 | 5/1999 |
| WO | WO-0076426 A2 | 12/2000 |
| WO | WO-0121061 A1 | 3/2001 |
| WO | WO-0189424 A1 | 11/2001 |
| WO | WO-0234158 A2 | 5/2002 |
| WO | WO-02084381 A2 | 10/2002 |
| WO | WO-02088830 A1 | 11/2002 |
| WO | WO-2004013680 A1 | 2/2004 |
| WO | WO-2004090611 A2 | 10/2004 |

OTHER PUBLICATIONS

Albert, Daniel M.; (Book Review) Intraocular Lenses: Evolution, Designs, Complications and Pathology, by David Apple et al., Arch Opthalomol. vol. 108, May 1990.
Alvarez S. L. et al., "Spectral threshold: measurement and clinical applications," British Journal of Ophthalmology, 1983, 67, 504-507.
Apple, David J. et al. "Intraocular Lens Evolution, Designs, Complications and Pathology", Williams & Wilkins, 1989, pp. 22-36 & pp. 205-221.
Artal et al., "Contributions of the cornea and the lens to the aberrations of the human eye," Optics Letters, 1998, 23 (21), 1713-1715.
Atchinson, "Design of aspheric intraocular lens," Ophthal Physiol Opt, 1991, 11, 137-146.
Atchinson, "Optical design of intraocular lenses," I On-axis performance Optometry & Vision Science, 1989, 66 (8), 492-506.
Atchinson, "Optical design of intraocular lenses," II On-axis performance Optometry & Vision Science, 1989, 66 (9), 579-590.
Atchinson, "Optical design of intraocular lenses," III On-axis performance Optometry & Vision Science, 1989, 66 (10), 671-681.
Atchinson, "Refractive errors induced by displacement of intraocular lenses within the pseudophakic eye," Optometry & Vision Science, 1989, 66 (3), 146-152.
Atchinson, "Third-order aberrations of pseudophakic eyes," Ophthal. Physiol. Opt., 1989, 9, 205-211.
Bonnet et al., "New method of topographical ophthalmometry—its theoretical and clinical applications," American Journal of Optometry and Archives of American Academy of Optometry, 1962, 39 (5), 227-251.
Buralli et al., "Optical performance of holographic kinoforms," Appl Opt, 1989, 28 (5), 976-983.
Cohen, "Diffractive bifocal lens designs," Optom Vis Sci, 1993, 70, 461-8.
Cohen, Allen L., "Practical design of a bifocal hologram contact lens or intraocular lens," Applied Optics, 1992, 31 (19), 3750-3754.
Dwyer W. O. et al., "Racial Differences in Color Vision: Do They Exist?," American Journal of Optometry & Physiological Optics, 1975, 52, 224-229.
El Hage et al., "Contribution of the crystalline lens to the spherical aberration of the eye," Journal of the Optical Society of America, 1973, 63 (2), 205-211.
Futhey J. A., "Diffractive bifocal intraocular lens," SPIE, 1989, 1052, 142-148.
Geun-Young et al., "Visual performance after correcting the monchromatic and chromatic aberrations of the eye," Journal of the Optical Society of America, 2002, 19 (2), 266-275.
Glasser A. et al., "Presbyopia and the optical changes in the human crystalline lens with age," Vision Res, 1998, 38 (2), 209-229.
Greivenkamp et al., "Visual acuity modeling using optical raytracing of schematic eyes," American Journal of Ophthalmology, 1995, 120 (2), 227-240.
Griswold Scott et al., "Scotopic Spectral Sensitivity of Phakic and Aphakic Observers Extending into the Near Ultraviolet," Vision res, 1992, 32 (9), 1739-1743.
Guillon et al., "Corneal topography: a clinical model," Ophthal. Physiol. Opt, 1986, 6 (1), 47-56.
Guirao Antonio et al., "Corneal wave aberration from videokeratography: accuracy and limitations of the procedure," Journal of Optical Society of America, 2000, 17 (6), 955-965.
Iovs, 1999, 40 (4), S535.
Kiely et al., "The mean shape of the human cornea," Optica ACTA, 1982, 29 (8), 1027-1040.
Kokoschka S. et al., "Influence of field size on the spectral sensitivity of the eye in the photopic and mesopic c range," American Journal of Optometry & Physiological Optics, 1985, 62 (2), 119-126.
Liang J. et al., "Objective measurement of wave aberrations of the human eye with the use of a Hartmann-Shack wave-front sensor," J Opt Soc Am A Opt Image Sci Vis, 1994, 11 (7), 1949-1957.
Lindsay et al., "Descriptors of corneal shape," Optometry and Vision Science, 1998, 75 (2), 156-158.
Lotmar, "Theoretical eye model with aspherics," Journal of the Optical Society of America, 1971, 61 (11), 1522-1529.
Malacara et al., "Wavefront fitting with discrete orthogonal polynomials in a unit radius circle," Optical Engineering, 1990, 29 (6), 672-675.
Mandell et al., "Mathematical model of the corneal contour," School of Optometry, University of California, 183-197.
Marcos Susana et al., "A new approach to the study of ocular chromatic aberrations," Vision Research, 1999, 39, 4309-4323.
Mordi et al., "Influence of Age of Chromatic Aberration of the Human Eye," American Journal of Optometry & Physiological Optics, 1985, 62 (12), 864-869.
Navarro et al., "Accommodation-dependent model of the human eye with aspherics," Journal of the Optical Society of America, 1985, 2 (8), 1273-1281.
Oshika et al., "Changes in corneal wavefront aberrations with aging," Investigative Ophthalmology & Visual Science, 1999, 40 (7), 1351-1355.
Patel et al., "Shape and radius of posterior corneal surface," Refractive and Corneal Surgery, 2006, 9, 173-181.
Said et al., "The Variation with Age of the Spectral Transmissivity of the Living Human Crystalline Lens," Gerontologia, 1959, 213-231.
Schwiegerlind et al., "Representation of videokeratoscopic height data with Zernike polynomials," Journal of the Optical Society of America, 1995, 12 (10), 2105-2113.
Seitz et al., "Corneal Topography," Current Opinion in Ophthalmolgy, 1997, 8 (4), 8-24.
Smith et al., "The spherical aberration of intra-ocular lenses," Ophthal. Physiol, 1988, 8, 287-294.
Smith G. et al., "The spherical aberration of the crystalline lens of the human eye," Vision Res., 2001, 41 (2), 235-243.
Smith Kinney, "Sensitivity of the eye to spectral radiation at scotopic and mesopic intensity levels," Journal of the Optical Society of America, 1955, 45 (7), 507-514.
Thibos L. N. et al., "The chromatic eye: a new reduced-eye model of ocular chromatic aberration in humans," Applied Optics, 1992, 31 (19), 3594-3600.
Thibos L. N. et al., "Theork and measurement of ocular chromatic aberration," Vision Res, 1988, 30 (1), 33-49.
Townsley, "New Knowledge of the corneal contour," 38-43.

Verriest G., "The Spectral Curve of Relative Luminous Efficiency in Different Age Groups of Aphakic Eyes," Mod Probl Ophthalmol., 1974, 13, 314-317.

Wang et al., "Wave-front interpretation with Zernike polynomials," Applied Optics, 1980, 19 (9), 1510-1518.

* cited by examiner

PRIOR ART

_US 7,984,990 B2_

OPHTHALMIC LENS WITH MULTIPLE PHASE PLATES

This application is a continuation of, and claims prior to, U.S. patent application Ser. No. 12/323,126, filed Nov. 25, 2008, which is a continuation of, and claims prior to, U.S. patent application Ser. No. 11/259,534, filed Oct. 25, 2005, now U.S. Pat. No. 7,455,404, the entire contents of each of which applications are hereby incorporated by reference in their entirety for all purposes as if fully set forth herein.

BACKGROUND OF THE INVENTION

1. Field of the Invention

This invention relates generally to an ophthalmic lens, and more specifically to multifocal ophthalmic lenses that combine both refraction and diffraction to provide an ocular image.

2. Description of the Related Art

Ophthalmic lenses, such as intraocular lenses (IOLs), phakic IOLs, and corneal implants, are used to enhance ocular vision. For instance, IOLs are now routinely used to replace the natural lens of an eye that is removed during cataract surgery. More recently, diffractive IOLs have been advantageously used to reduce lens thickness and correct for presbyopia. For instance, diffractive bifocal lenses divide incident light into two diffractive orders to provide both near and distance vision. The use of diffractive optics in ophthalmic lenses is described by Cohen in U.S. Pat. Nos. 4,881,804; 4,881,805; 4,995,714; 4,995,715; 5,017,000; 5,054,905; 5,056,908; 5,117,306; 5,120,120; 5,121,979; 5,121,980; and 5,144,483, which are all herein incorporated by reference. Freeman also describes the use of diffractive optics in ophthalmic lenses in U.S. Pat. Nos. 4,637,697; 4,641,934; 4,642,112; 4,655,565; and 5,748,282, which are also herein incorporated by reference.

In such lenses, the optic area is generally divided into a plurality of annular zones or echelettes that are offset parallel to the optical axis by predetermined step heights to provide a specific phase relationship between the zones. The term "zone plate," or "phase plate," as used herein and as is generally recognized in the art, is defined to be a pattern of concentrically arranged annular zones which is characterized, at least in part, by the step height between zones, the circumferential spacing between zones, and the surface profile of each zone. Zone plates are usually configured to maintain a predefined phase relationship of light passing through the zones. In addition to Cohen and Freeman, Futhey also describes various ophthalmic diffractive lenses, for example, in U.S. Pat. Nos. 4,936,666; 5,129,718; and 5,229,797, herein incorporated by reference.

In one approach, a phase plate or zone plate comprises a plurality of zones in which the optical height of the steps (i.e., the physical height times the difference between the refractive index of the material and the refractive index of the surrounding media) between the individual zones is one-half that of light at a design wavelength in the visible range. In such designs, approximately 80% of the light at the design wavelength is evenly split between zeroth and first diffraction orders, where the zeroth diffraction order is generally considered to be light that is un-diffracted or unaffected by the zone plate. This zone plate configuration is used to produce a bifocal lens in which (1) the zeroth diffraction order produces a first focus or focal point for distant vision and (2) the first diffraction order produces a second focus or focal point corresponding to near or intermediate vision. In addition, chromatic dispersion produced by the first diffraction order, which is usually opposite in sign to refractive chromatic dispersion, may be used to reduce the overall chromatic aberrations in the near vision focus, since the refractive and diffractive chromatic dispersions components tend to cancel one another. However, the distant vision focus does not benefit from this diffractive chromatic dispersion, since it comprises only light that is un-diffracted by the zone plate. Thus, the distance vision is purely refractive and receives no reduction in any chromatic aberrations induced by refractive chromatic dispersions.

A characteristic of ophthalmic lenses incorporating diffractive zones or phase plates is that the amount of light in the near and distant foci is substantially constant for all pupil sizes. It is desirable in certain instances to increase the amount of light in the distant focus as the pupil size increases, for instance under intermediate or low light conditions. One way to increase the amount of light dedicated to distance vision is to restrict the zone plate to the central portion of the lens and to make the outer region of the lens refractive only, as disclosed in Cohen '804. Another approach is disclosed by Lee et al. in U.S. Pat. No. 5,699,142, herein incorporated by reference. Lee et al. teaches a diffractive lens comprising an apodization zone in which the step height between zones in the transition region is progressively reduced. The steps between zones are centered on a base curve BC so as to avoid sharp discontinuities in the resulting wavefront that can produce unwanted diffractive effects. In either of these designs, the outer refractive portion of the lens does not benefit from the use of diffractive power to reduce chromatic aberrations, potentially resulting in increased chromatic aberrations as the pupil size increases under lower lighting conditions.

One problem associated with multifocal/bifocal IOLs is the problem of halos. This problem manifests itself when light from the unused focal image creates an out-of-focus image that is superimposed on the used focal image. For example, if light from a distant point source or slightly extended source is imaged onto the retina of the eye by the distant focus produced by a bifocal IOL, the near focus produced by the IOL will simultaneously superimpose a defocused image on top of the image formed by the IOL's distant focus. This defocused image may manifest itself in the form of a ring of light surrounding the in-focus image produced by the IOL's distant focus.

Devices and method are needed to improve the performance of diffractive lenses in ophthalmic applications.

SUMMARY OF THE INVENTION

One aspect of the present invention involves an ophthalmic lens comprising an optic having an anterior surface, a posterior surface, and an optical axis. The ophthalmic lens further comprises a first region having a first optical power and a second region having a second optical power. The first region comprises a multifocal phase plate configured for forming a first focus and a second focus, while the second region comprises a monofocal phase plate for forming a third focus. The monofocal phase plate and the multifocal phase plate are preferably disposed about at least one base curvature. In certain embodiments, the first region comprises a first base curvature having a finite first radius of curvature and the second region comprises a second base curvature having a finite second radius of curvature different from the first radius of curvature. The ophthalmic lens may further comprise a third region having a third optical power and comprising a third phase plate. For example, the third region may be an intermediate region that is disposed between the monofocal phase plate and the multifocal phase plate.

In one embodiment the first region is disposed in the center of the optic and the second region is disposed outside the first region. Alternatively, the second region is disposed in the center of the optic and the first region is disposed outside the second region. In either embodiment, the base curvature may have a shape that is spherical, parabolic, elliptical, hyperbolic, or some other aspherical shape. The first region may have a refractive optical power that is preferably greater than a diffractive optical power of the multifocal phase plate and the second region may have a refractive optical power that is preferably greater than a diffractive optical power of the monofocal phase plate.

The monofocal phase plate and the multifocal phase plate may both be disposed on the anterior surface of the optic or on the posterior surface of the optic. Alternatively, the monofocal phase plate and the multifocal phase plate may be disposed on opposite surfaces of the optic.

In another aspect of the invention, at least one of the multifocal phase plate and the monofocal phase plate comprises a plurality of concentric zones and a step along the optical axis between adjacent zones. Alternatively, at least one of the multifocal phase plate and the monofocal phase plate has a variation in refractive index across the surfaces thereof. Preferably, the variation in refractive index across the surfaces is in a radial direction from the center of the optic, although other configurations are also possible. Such a variation in refractive index may be produced, for instance, by a phase hologram.

The multifocal phase plate may be a bifocal phase plate such as a MOD 0.5 phase plate or MOD 1.5 phase plate or, more generally, a MOD x.5 phase plate, where x is an integer. The monofocal phase plate may be a MOD 1 phase plate, a MOD 2 phase plate or, more generally, a MOD y.0 phase plate, where y is an integer. Other types of phase plates may also be used that, for example, produce one or more negative diffraction orders.

In a particularly useful aspect of the invention, the first region comprises a first base curvature having a first radius of curvature and the second region comprises a second base curvature having a second radius of curvature, the first radius of curvature being different from the second radius of curvature. Additionally, the multifocal phase plate may be a MOD 0.5 phase plate and monofocal phase plate may be a MOD 1 phase plate. In this configuration, the first focus corresponds to a zeroth diffraction order of the multifocal phase plate, the second focus corresponds to a first diffraction order of the multifocal phase plate, and the third focus corresponds to a first diffraction order of the monofocal phase plate.

The first focus may be used to provide distant vision and the second focus may be used to provide near vision or intermediate vision. The second base curvature may be configured such that the third focus is disposed at substantially the same location as either the first focus, the second focus, between the first and second focus, or some other location that is different from either the first or second focus. Either or both of the multifocal phase plate and the monofocal phase plate may be adapted to adjust chromatic aberrations in the second and/or third foci. Similarly, the monofocal phase plate, the second base curvature, or both may be configured to reduce spherical or other aberrations produced by first region in at least one of the first focus and the second focus.

In an additional aspect of the invention, an ophthalmic lens comprises an optic having an anterior surface, a posterior surface, and an optical axis, a first region and a second region. The first region comprises a first phase plate disposed on a first base curvature with a finite first radius of curvature. The second region comprising a second phase plate disposed on a second base curvature with a finite second radius of curvature. In addition, the first radius of curvature may be different from the second radius of curvature.

In another aspect of the present invention, an ophthalmic lens comprises an optic having an anterior surface, a posterior surface, and an optical axis. The ophthalmic lens further comprises a first region having a first refractive optical power, where the first region comprises (1) a first base curvature having a first radius of curvature and (2) a multifocal phase plate for forming a first focus and a second focus disposed closer to the optic than the first focus. The ophthalmic lens also comprises a second region having a second refractive optical power, where the second region comprises (1) a second base curvature having a second radius of curvature different from the first radius of curvature and (2) a monofocal phase plate for forming a third focus. Preferably, the first radius of curvature and the second radius of curvatures are both finite so that the first region and the second region both have refractive optical power.

In yet another aspect of the present invention, an ophthalmic lens comprises an optic having an anterior surface, a posterior surface, and an optical axis. The ophthalmic lens further comprises a first region having a first refractive optical power, the first region comprising a multifocal phase plate disposed on a first base curvature having a first radius of curvature. The ophthalmic lens also comprises a second region having a second refractive optical power, the second region comprising a monofocal phase plate disposed on a second base curvature having a finite second radius of curvature different from the first radius of curvature. Preferably, the first radius of curvature and the second radius of curvatures are both finite so that the first region and the second region both have refractive optical power.

In one aspect of the present invention, an ophthalmic lens comprises an optic having an anterior surface, a posterior surface, a first base curvature, and an optical axis. The ophthalmic lens further comprises a multifocal phase plate configured to direct light to a first focus and a second focus, the multifocal phase plate comprising a first plurality of echelettes centered about a first base curvature in a direction that is parallel to the optical axis, the first base curvature having a first radius of curvature. The ophthalmic lens also comprises an intermediate phase plate surrounding the multifocal phase plate and configured to change the overall resultant amplitude and/or distribution of light directed to the second focus, the intermediate phase plate comprising a second plurality of echelettes centered about the first base curvature or about a second base curvature having a second radius of curvature different from the first radius of curvature. The ophthalmic lens additionally comprises an outer refractive region having a refractive optical power and no diffractive optical power, the outer refractive region surrounding the intermediate phase plate and configured to direct light to the first focus.

In some embodiments, the first plurality of echelettes comprises a first step height between adjacent echelettes the second plurality of echelettes comprises a second step height between adjacent echelettes. The second step height may be less than the first step height. In certain embodiments, the first step height is determine by the equation $0.5 \times \lambda/(n2-n1)$ and the second step height is determine by the equation $B \times \lambda/(n2-n1)$, where:

B is a constant,
$\lambda$ is a design wavelength,
n2 is the refractive index of the ophthalmic lens,
n1 is the refractive index of the media adjacent the phase plates.

wherein B may be about 0.25, about 0.75, or some other value greater than or less than 1. In one embodiment the second plurality of echelettes comprises 4 echelettes, although any number of echelettes may be used. In other embodiment, second plurality of echelettes may comprise a first step height between one or more adjacent echelettes and a second step height between one or more adjacent echelettes. In such embodiments, the first step height may be determined by the equation $0.375 \times \lambda/(n2-n1)$, and the second step height is determined by the equation $0.125 \times \lambda/(n2-n1)$.

In yet another aspect of the present invention, an ophthalmic lens comprises an optic having an anterior surface, a posterior surface, and an optical axis. The ophthalmic lens further comprises a multifocal phase plate, a monofocal phase plate, an intermediate phase plate located between the multifocal phase plate and the monofocal phase plate. The multifocal phase plate may be configured to direct light to a first focus and a second focus. The multifocal phase plate further comprises a first plurality of echelettes disposed on a first base curvature having a first radius of curvature. The monofocal phase plate comprises a second plurality of echelettes disposed on a second base curvature having a second radius of curvature different from the first radius of curvature. The intermediate phase plate comprises a third plurality of echelettes disposed on a third base curvature having a third radius of curvature and configured to change the overall resultant amplitude and/or distribution of light directed to the second focus.

The third radius of curvature of the ophthalmic lens may equal to the first radius of curvature or may be greater than or less than the first radius of curvature. The multifocal phase plate and the intermediate phase plates generally produce a halo image in a plane containing the first focus.

In certain embodiments, the first plurality of echelettes comprise a first step height between adjacent echelettes and the second plurality of echelettes comprises a second step height between adjacent echelettes. The second step height may be less than the first step height. The first step height may be determine by the equation $0.5 \times \lambda/(n2-n1)$ and the second step height may be determine by the equation $B \times \lambda/(n2-n1)$, where:

B is a constant,
$\lambda$ is a design wavelength,
n2 is the refractive index of the ophthalmic lens,
n1 is the refractive index of the media adjacent the phase plates.
wherein B may be about 0.25, about 0.75, or some other value greater than or less than 1. In one embodiment the second plurality of echelettes comprises 4 echelettes, although any number of echelettes may be used. In certain embodiments, the second plurality of echelettes comprises a first step height between one or more adjacent echelettes and a second step height between one or more adjacent echelettes. In such embodiments, the first step height is determined by the equation $0.375 \times \lambda/(n2-n1)$, and the second step height is determined by the equation $0.125 \times \lambda/(n2-n1)$. In other embodiments, the first plurality of echelettes comprises a first step height between adjacent echelettes the second plurality of echelettes comprises a plurality of different step heights between adjacent echelettes and the plurality of different step heights each are less than the first step height. Alternatively, the plurality of different step heights progressively decrease as the distance from the optical axis increases.

In another aspect of the present invention, an ophthalmic lens provides a plurality of foci and includes an optic having an anterior surface, a posterior surface, and an optical axis. The ophthalmic lens has a first region and a second region. The first region has a first refractive optical power and includes a first base curvature having a finite first radius of curvature and a first phase plate having at least one diffraction order with a diffractive optical power. The first region is configured for forming a first focus and a second focus. The second region has a second refractive optical power and includes a second base curvature having a finite second radius of curvature that is different from the first radius of curvature and a second phase plate having at least one diffraction order with a diffractive optical power. The second region is configured for forming a third focus that is between the first focus and the second focus. The ophthalmic lens may be configured so the first focus provides distant vision, the second focus provides near vision, and the third focus provides intermediate vision.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 19 figures, with like numerals indicating like parts.

DETAILED DESCRIPTION OF THE DRAWINGS

Embodiments of the present inventions are directed to a multifocal ophthalmic lens (e.g., an intraocular lens (IOL), phakic IOL, and corneal implant) comprising a plurality of surface regions having both a refractive optical power and a diffractive optical power that together provide enhanced ocular vision. The terms "power" or "optical power", as used herein, mean the ability of a lens, an optic, an optic surface, or at least a portion of an optic surface to redirect incident light for the purpose of forming a real or virtual focus or focal point. The optical power may result from reflection, refraction, diffraction, or some combination thereof and is generally expressed in units of Diopters. One of skill in the art will appreciate that the optical power of a surface, lens, or optic is generally equal to the reciprocal of the focal length of the surface, lens, or optic when the focal length is expressed in units of meters. As used herein, the term "refractive optical power" or "refractive power" means optical power produced by the refraction of light as it interacts with a surface, lens, or optic. As used herein, the term "diffractive optical power" or "diffractive power" means optical power resulting from the diffraction of light as it interacts with a surface, lens, or optic, for example as produced by a diffraction order of a phase plate. When used in reference to a phase plate, the term "diffractive optical power" or "diffractive power" means the substantially equivalent optical power attributed to a refractive lens that converges or diverges light at a design wavelength in substantially the same manner as the diffractive phase plate for which the term is used.

Figure 1:
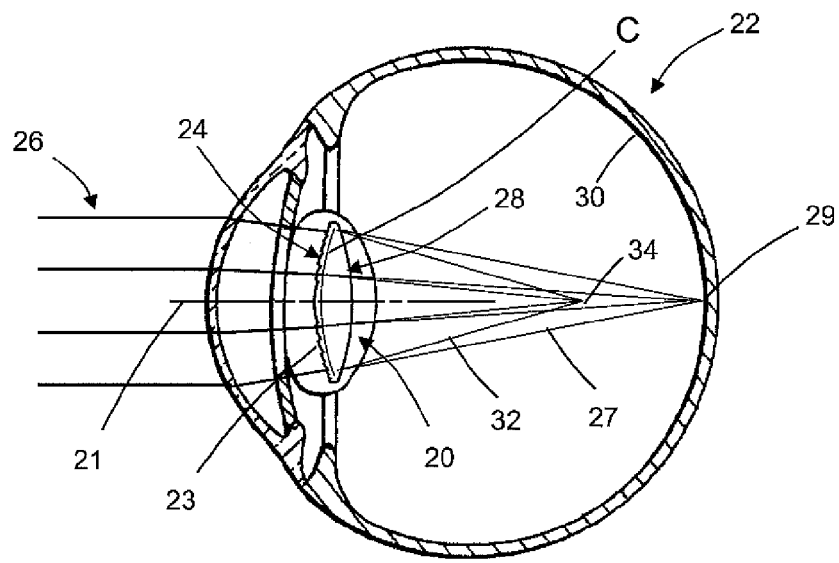
FIG. 1 is a side view of a prior art bifocal intraocular lens illustrating how light from a distant object is focused onto the retina of an eye.

FIG. 1 illustrates a prior art bifocal IOL 20 with an optical axis 21 disposed in an eye 22. The IOL 20 comprises phase plate 23 made, for example, in accordance with the teachings of Freeman in U.S. Pat. No. 4,642,112 or Cohen in U.S. Pat. No. 5,144,483. The phase plate 23 is disposed on an anterior surface 24 having a base curvature C and is illuminated by incident light 26 from a distant object that enters the eye 22 in the form of collimated light. A first portion 27 of the incident light 26 is substantially unaffected by the phase plate 23 and is focused by the anterior surface 24 and a posterior surface 28 through refraction to produce a first focus 29 approximately located on a retina 30 of the eye 22 for providing distant vision. A second portion 32 of the incident light 26 is diffracted by the phase plate 23 to form a second focus 34 for providing near or intermediate vision. The net optical power of the anterior surface 24 for forming the second focus 34 is generally considered to be a combination of (1) a refractive optical power of the anterior surface 24 due to the base curvature C and (2) a diffractive optical power of the phase plate 23. It will be appreciated that in an actual eye, the light forming the second focus 34 would continue propagating towards the retina 30; however, this light is illustrated as terminating at the second focus 34 for purposes of clarity.

The term "near vision," as used herein, refers to vision provided by at least a portion of a lens, such as the IOL 20, or an imaging system, wherein objects relatively close to the subject are substantially in focus on the retina of the eye of a subject. The term "near vision' generally corresponds to vision provided when objects are at a distance between about 25 cm to about 50 cm. Conversely, the term "distant vision," as used herein, refers to vision provided by at least a portion of a lens or imaging system, wherein objects relatively far from the subject are substantially on the retina of the eye. The term "distant vision" generally corresponds to vision provided when objects are at a distance of at least about 1 meter to about 2 meters away from the subject, preferably at a distance of 5 to 6 meters or greater. The term "intermediate vision" generally refers to vision provided by at least a portion of a lens or imaging system, wherein objects at an intermediate distance from the subject are substantially in focus on the retina of the eye. Intermediate vision generally corresponds to vision provided when objects are at a distance of about 40 centimeters to about 1.5 meters.

Referring again to FIG. 1, the IOL 20 effectively has two optical powers due to the combination of the anterior surface 24, the posterior surface 28, and the phase plate 23. It will be appreciated that the IOL 20 may have additional optical powers since the incident light 26 would normally be diffracted into other higher and lower diffraction orders. For instance, when the phase plate 23 is made according to the teachings of Cohen in the '483 patent, approximately 80% of the light at a design wavelength is approximately evenly split between a zeroth diffraction order and a first diffraction order, while the remaining 20% of the light is split between higher diffraction orders (e.g., greater than a +1 diffraction order) and/or lower diffraction orders (e.g., less than or equal to a −1 diffraction order) of the phase plate 23.

Figure 2:
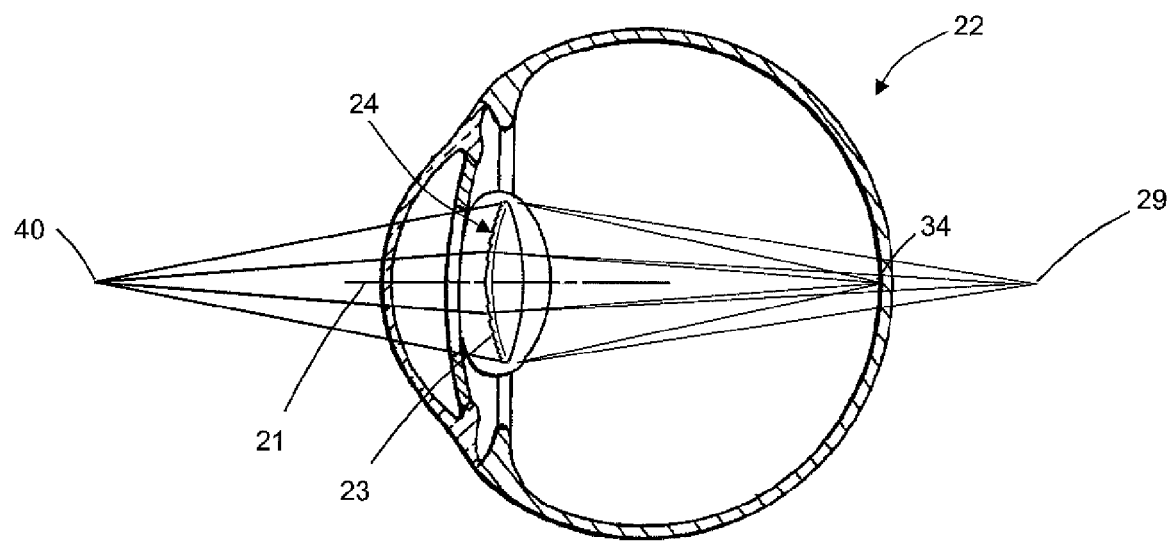
FIG. 2 is a side view of a prior art bifocal intraocular lens illustrating how light from a near point source object is focused onto the retina of an eye.

FIG. 2 illustrates the performance of the IOL 20 for a near object 40 located relatively close to the eye 22. Under these conditions, the distant and near foci 29, 34 are disposed such that the near focus 34 is approximately located on the retina 30 and the distant focus 29 is located behind the retina 30. Therefore, the IOL 20 may function as a bifocal lens that provides a patient with both near vision and distant in a way that at least approximates the accommodative ability of the natural lens lost due to presbyopia and/or removal of the natural lens.

The phase plate 23 of the bifocal IOL 20 generally comprises a plurality of annular zones, facets, or echelettes having a particular offset or step height between adjacent zones along the optical axis 21. As used herein, the terms "zone", "facet", or "echelette" are used interchangeably to mean portions of a zone or phase plate disposed between steps or other phase discontinuity thereon.

The bifocal characteristics of the IOL 20 may be realized by selecting the step height between adjacent zones to be such that rays to either side of the step experience a difference in optical path length of λ/2, where λ is a design wavelength. For instance, if the bifocal IOL 20 is made of material having a refractive index of $n_{IOL}$ and the material adjacent to the anterior surface 24 is $n_o$, then the step height $h_{step}$ is given by the relationship:

$$h_{step} = \frac{\lambda}{2(n_{IOL} - n_o)}, \qquad (1)$$

herein referred to as a λ/2 phase plate. The height of the step may also be referred to herein by its phase height. For example, the step height $h_{step}$ given by Equation (1) will be referred to as a λ/2 phase step height. As will be appreciated by those of skill in the art, a λ/2 phase plate may be used to produce zeroth and first diffraction order containing approximately 40% each of the total light diffracted by the phase plate. This type of phase plate may be referred to as a MOD 0.5 phase plate, indicating that the step height corresponds to an optical path length difference of 0.5 times the design wavelength λ.

Alternatively, the IOL 20 may be in the form of a monofocal IOL in which the step height is such that rays to either side of the step between adjacent zones experience a difference in optical path length of λ. Such a phase plate will be herein referred to as a 1λ phase plate and as having a 1λ phase step height. Thus, for the material refractive indices just used, a step height given by the relationship:

$$h_{step} = \frac{\lambda}{(n_{IOL} - n_o)}, \qquad (2)$$

provides a monofocal IOL in which essentially 100% of the energy in the incident light 26 is diffracted into the first diffraction order of the phase plate 23 and, therefore, into the near focus 34. This type of phase plate may be referred to as a MOD 1 phase plate, indicating that the step height corresponds to an optical path length difference of one times the design wavelength λ.

The phase plate 23 may alternatively be constructed so that the step height between adjacent zones is such that rays to either side of the step experience a difference in optical path length of 3λ/2, as taught by Futhey in U.S. Pat. No. 5,229,797. In this case the location of the distant and near foci 29, 34 are provided by the combination of the refractive powers of the anterior and posterior surfaces 24, 28 and the first and second diffraction orders of the phase plate 23. This type of phase plate may be referred to as a MOD 1.5 phase plate, indicating that the step height corresponds to an optical path length difference of 1.5 times the design wavelength λ. Higher MOD phase plates are taught by Faklis et al. in U.S. Pat. No. 5,589,982, which is herein incorporated by reference.

Based on this convention, a MOD x.5 phase plate, where x is an integer, is a phase plate with a step height between adjacent zones corresponding to an optical path length difference of (x+½) times the design wavelength λ, where x is an integer greater than or equal to one. MOD x.5 phase plates are characterized in that most of the energy from light incident on the phase plate is generally split between two diffraction orders. A MOD x phase plate refers to one in which the step height between adjacent zones corresponds to an optical path length difference of x times the design wavelength λ, where x is an integer greater than or equal to one. MOD x phase plates are characterized in that most or all of the energy from incident light is contained in a single diffraction order. This same convention can also be applied to phase plates having no physical step height between adjacent zones. For example, the phase plate 23 could be produced using holographic or other such methods to form of a MOD x phase plate in which phase change between adjacent zones is the same as that produced by a substantially equivalent phase plate having a step height between adjacent zones corresponding to an optical path length difference of x times the design wavelength λ. Alternatively, the various zones may be provided in the form of a transmission grating.

Figure 3:
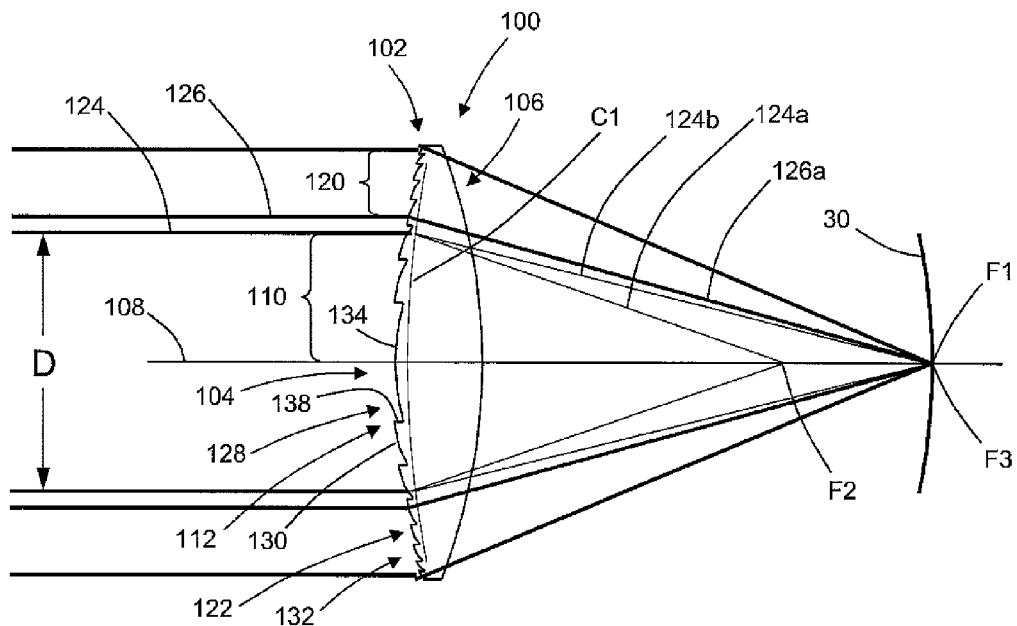
FIG. 3 is a side view of one embodiment of a diffractive ophthalmic lens according to the invention comprising a plurality of diffractive phase plates, wherein a peripheral phase plate is configured to provide distant vision.

Referring to FIG. 3, in certain embodiments of the present invention, an ophthalmic lens 100 comprises an optic 102. The optic 102 has an anterior surface 104, a posterior surface 106, and an optical axis 108. The optic 102 comprises a first region 110 having an optical power and comprising a multifocal phase plate 112 for providing, producing, or forming a first focus or focal point F1 and a second focus or focal point F2. The optic 102 further comprises a second region 120 having an optical power and comprising a monofocal phase plate 122 for providing, producing, or forming a third focus F3. As a general convention, light rays produced by the interaction of light from an object with a bifocal or multifocal phase plate, such as the multifocal phase plate 112, are represented in the figures by lighter weight lines than those light rays produced by the interaction of light from an object with a monofocal phase plate, such as the monofocal phase plate 122. For example, an input light ray 124 illustrated in FIG. 3 is split into two focused light rays 124a and 124b directed to the first focus F1 and the second focus F2, respectively, which are represented by lighter weight lines. By contrast, an input light ray 126 illustrated in FIG. 3 produces a single focused light ray 126a that is directed to the third focus F3, which is represented by heavier weight line.

The ophthalmic lens 100 may be an intraocular lens for placement in either the posterior or anterior chambers of a mammalian eye. As such, the ophthalmic lens 100 may be used to replace the natural lens of the eye, for example after removal of the natural lens during cataract surgery. Alternatively, the ophthalmic lens 100 may be a phakic lens that is disposed either in front of the iris, behind the iris, or in the plane defined by the iris. Alternatively, the ophthalmic lens 100 may be a corneal implant that is, for example, inserted within the stromal layer of the cornea. The ophthalmic lens 100 may also be a contact lens or some other type of ophthalmic device that is used to provide or improve the vision of a subject. The ophthalmic lens 100 may also be used as part of an imaging system, for example to supplement or correct a previously implanted IOL or corneal implant, or in an accommodating lens system similar to that disclosed by Lang et al. in U.S. Pat. No. 6,231,603, herein incorporated by reference.

The ophthalmic lens 100 may be constructed of any of the commonly employed material or materials used for rigid optics, such as polymethylmethacrylate (PMMA), or of any of the commonly used materials for resiliently deformable or foldable optics, such as silicone polymeric materials, acrylic polymeric materials, hydrogel-forming polymeric materials, such as polyhydroxyethylmethacrylate, polyphosphazenes, polyurethanes, and mixtures thereof and the like. The material preferably forms an optically clear optic and exhibits biocompatibility in the environment of the eye. The ophthalmic lens 100 may be made of or contain materials useful for forming the phase plates 112, 122 such as photosensitive materials (e.g., photopolymer or silver halide) or a variable refractive index material. Portions of the optic 102 may be constructed of a more opaque material, for example to selectively block light at the boundaries between the phase plates 112, 122 or between adjacent zones of within the phase plates 112, 122. Such material might serve to reduce scattered light or to otherwise define or modify the performance of either or both of the phase plates 112, 122.

The selection of suitable lens materials is well known to those of skill in the art. See, for example, David J. Apple, et al., Intraocular Lenses: Evolution, Design, Complications, and Pathology, (1989) William & Wilkins. Foldable/deformable materials are particularly advantageous since optics made from such deformable materials may be rolled, folded or otherwise deformed and inserted into the eye through a small incision. The lens material preferably has a refractive index allowing a relatively thin, and preferably flexible optic section, for example, having a thickness in the range of about 150 microns to about 1000 microns, and preferably about 150 microns or about 200 microns to about 500 microns. When the ophthalmic lens 100 is an intraocular lens, the optic 102 may have a diameter of about 4 mm or less to about 7 mm or more, preferably about 5.0 mm to about 6.0 mm or about 6.5 mm.

When configured as an IOL, the ophthalmic lens 100 may comprise any of the various means available in the art for centering or otherwise disposing the optic 102 within the eye. For example, ophthalmic lens 100 may comprise one or more fixation members or haptics. The haptics may be made of the same material as the optic 102 and/or integrally formed therewith to form a one-piece IOL. Alternatively, one or more haptics may be formed separately and attached to the optic 102 to provide a multi-piece configuration. The fixation members may comprise any of a variety of materials which exhibit sufficient supporting strength and resilience, and/or which are substantially biologically inert in the intended in vivo or in-the-eye environment. Suitable materials for this purpose include, for example, polymeric materials such as silicone polymeric materials, acrylic polymeric materials, hydrogel-forming polymeric materials, such as polyhydroxyethylmethacrylate, polyphosphazenes, polyurethanes, and mixtures thereof and the like. In other embodiments, the ophthalmic lens 100 comprises a positioning means that allows the optic 102 to move along the optical axis 108 in response to deformation of the capsular bag and/or in response to the ciliary muscles of the eye.

In certain embodiments, the monofocal phase plate 122 and the multifocal phase plate 112 are both disposed on the anterior surface 104, as shown in FIG. 3. Alternatively, the monofocal phase plate 122 and the multifocal phase plate 112 are both disposed on the posterior surface 106. In other embodiments, the monofocal phase plate 122 and the multifocal phase plate 112 are be disposed on opposite surfaces 104, 106 of the optic 102. For example, the multifocal phase plate 112 may be disposed on the anterior surface 104, while the monofocal phase plate 122 is disposed on the posterior surface 106.

The first region 110 with the multifocal phase plate 112 may be disposed in the center of the optic 102 and the second region 120 with the monofocal phase plate 122 may be disposed outside the first region 110. Alternatively, the second region 120 may be disposed in the center of the optic 102 and the first region 110 may be disposed outside the second region 120. The phase plates 112, 122 preferably each have a circular outer diameter when viewed from the front.

The multifocal phase plate 112 may comprise a first plurality 128 of diffraction zones, facets, or echelettes 130, while the monofocal phase plate 122 comprises a second plurality 132 of diffraction zones 130. The first region 110 typically includes a central diffraction zone 134 that is substantially circular and is surrounded by the remaining diffractive zones 130 that typically have an annular shape. Determination of the outer diameter of each of the diffraction zones 130 is well known in the art and is generally a function of a design wavelength λ, and the desired focal length of the lens. The design wavelength λ may be anywhere within the electromagnetic spectrum, for example in visible, infrared or ultraviolet wave bands. The design wavelength λ is generally in the visible waveband and is preferably in the range of approximately 400 nm to approximately 800 nm, more preferably in the range of approximately 500 nm to approximately 600 nm, even more preferably in the range of 540 nm to 560 nm. In some embodiments, the design wavelength λ is approximately 500 nm, approximately 546 nm, or approximately 550 nm.

When the multifocal phase plate 112 is disposed in the center of the optic 102, as illustrated in FIG. 3, the multifocal phase plate 112 has an outer diameter D. Each of the diffraction zones 130 preferably have an area that is substantially the same as each of the remaining diffractive zones 130; however, the central zone 134 may optionally have an area that is either less than or greater than the area of the remaining annular diffractive zones 130 as taught, for example, by the Futhey '718 patent or the Cohen '980 patent.

When the ophthalmic lens 100 is an IOL, the diameter D may be selected such that the iris of the eye substantially prevents light from passing through the monofocal phase plate 122 under bright lighting conditions. The outer diameter D is preferably less than approximately 5 mm, more preferably less than less than about 4 mm. In certain embodiments, the design wavelength λ is approximately 550 nm and the outer diameter D is approximately 3.0 mm in diameter and comprises 8 diffraction zones 130, including the central diffraction zone 134. In other embodiments, the outer diameter D is approximately 3.3 mm, 3.6 mm, or 3.9 mm and comprises 10, 12, or 14 diffraction zones 130, respectively.

The diffractive zones 130 are preferably offset parallel to the optical axis 108 so as to form steps 138 between adjacent zones 130, the steps 138 being selected to produce a predefined phase relationship between each of the diffractive zones 130. The size of the steps 138 between adjacent zones 130 in the multifocal phase plate 112 are preferably different from the size of the steps 138 between adjacent zones 130 in the monofocal phase plate 122. In certain embodiments, the diffractive zones 130 are formed by refractive index variations within the first region 110, the second region 120, or both so as to provide a predetermined phase relationship between the various zones 130 of the multifocal and/or monofocal phase plates 112, 122. The use of material and methods discussed above herein may be used to form the diffractive zones 130 so as to eliminate, or at least reduce the size of, the steps 138 between adjacent zones 130. Preferably, the variation in refractive index across the surfaces is in a radial direction from the center of the optic. A predetermined refractive index variation may be produced when either the multifocal phase plate 112 or the monofocal phase plate 122 is a phase hologram. Such holograms may be produced using a material such as photopolymer or silver halide, in which the refractive index may be varied by exposure to a holographically formed interference pattern. Other means for producing the phase plates 112, 122 are also anticipated and consistent with embodiments of the ophthalmic lens 100. The hologram could alternatively take the form of a transmission hologram in which the transmission varies with distance from the optical axis.

The multifocal phase plate 112 and monofocal phase plate 122 may be disposed on or about a base curvature C1 such that the regions 110, 120 have a refractive optical power that is separate from a diffractive optical power produced by the phase plates 112, 122. As illustrated in FIG. 3, the refractive optical power of regions 110, 120 may be produced by forming the ophthalmic lens 100 as a biconvex lens; however, other lens forms may be used such as, for example, a plano-convex, plano-concave, concave-concave, or meniscus lens. In addition, the optical power of the ophthalmic lens 100 may be either positive or negative. For example, when the ophthalmic lens 100 is an IOL for a pseudophakic eye, the IOL will generally have a positive optical power; however, when the ophthalmic lens 100 is used as a phakic IOL (e.g., one used in an eye containing the natural lens), the IOL can have either a positive or negative optical power, depending on the ocular condition being corrected.

The overall profile or shape of the anterior surface 104 and the posterior surface 106 may be any that is commonly used for producing an optic based on refraction of incident light. For instance, the overall shape or profile of the anterior surface 104, as represented by the base curvature C1, may be spherical with an overall radius of curvature R1 (not shown) that is generally finite (i.e., is not flat or substantially flat, that is with surface deviations on the order of about a wavelength of visible light or less). The detailed profile of the anterior surface 104 in the area of the first region 110 is the summation of the base curvature C1 and the profile of the multifocal phase plate 112. Similarly, the detailed profile of the anterior surface 104 in the area of the second region 120 is the summation of the base curvature C1 and the profile of the monofocal phase plate 122.

Alternatively, the overall profile or shape of either the anterior surface 104, the posterior surface 106, or both the surfaces 104, 106 may be parabolic, elliptical, hyperbolic, or any aspheric shape common in the art, for example, for reducing aberrations such as spherical aberrations or astigmatism. For example, the posterior surface 106 may be an aspheric surface designed to reduce spherical aberrations based on either an individual cornea or group of corneas as described by Piers et al. in U.S. Pat. Nos. 6,609,673 and 6,830,332 and U.S. patent application Ser. No. 10/724,852, all herein incorporated by reference. Other aspheric and asymmetric surface profiles of the anterior surface 104 and the posterior surface 106 of use within the art are also consistent with embodiments of the ophthalmic lens 100. For example, the posterior surface 106, or both the surfaces 104, 106 may be defined as having a central lens radius of R1 and a conic constant of k. In such embodiments, the surface profile z may, in a non-limiting example, be defined by the equation:

$$z = \frac{\left(\frac{1}{R1}\right)r^2}{1+\sqrt{1-(1+k)\left(\frac{1}{R1}\right)^2 r^2}} + a_4 r^4 + a_6 r^6 + \ldots, \quad (3)$$

where r is the radial distance from the optical axis and z the sag in the direction of light propagation, and $a_4, a_6 \ldots$ are coefficients.

The refractive optical power of the first and second regions 110, 120 are preferably within a range of about −10 Diopters to at least about +50 Diopters, more preferably within a range of at least about +10 Diopters to at least about +40 Diopters, and most preferably within a range of at least about +10 Diopters to at least about +30 Diopters. The most preferred range is typical of IOLs used in aphakic eyes, for instance after cataract surgery. When the ophthalmic lens 100 is a phakic IOL (an IOL used in an eye still having the natural lens), the refractive optical power of the first and second regions 110, 120 are preferably within a range of at least about −30 Diopters to at least about +30 Diopters, more preferably within a range of at least about −20 Diopters to at least about +20 Diopters, and even more preferably within a range of at least about −10 Diopters to at least about +10 Diopters. Other ranges of the refractive optical power may be preferred, depending on the particular application and type of ophthalmic lens to be used.

Preferably, the refractive optical power of the first and second regions 110, 120 are much greater than the diffractive optical powers of the multifocal phase plate 112 and/or the monofocal phase plate 122. For example, if the ophthalmic lens 100 is an IOL for a pseudophakic eye, the refractive optical power of the first and second regions 110, 120 is preferably at least about 10 Diopters to at least about 40 Diopters, while the multifocal and monofocal phase plates 112, 122 have at least one diffraction order, for instance a first diffraction order, with a diffractive optical power of at least about +2 Diopters to at least about +6 Diopters, preferably about +4 Diopters.

The total optical power of the second region 120 may be regarded as the summation of the refractive optical power of the second region 120 and the diffractive optical power of the monofocal phase plate 122. For instance, if the refractive optical power is 30 Diopters and the diffractive optical power is +4 Diopters, the total optical power of the second region 120 would be approximately 34 Diopters. Because the multifocal phase plate 112 produces at least two diffraction orders, the first region 110 may be considered as having at least two effective optical powers. For instance, the first region 110 may be configured to have a refractive optical power of 30 Diopters and a multifocal phase plate 112 that produces a zeroth diffraction order having no optical power and a first diffraction order having a diffractive optical power of +4 Diopters. Using this configuration, the multifocal phase plate 112 may be considered as having a first effective optical power that is approximately equal to the refractive optical power of 30 Diopters and a second effective optical power of 34 Diopters, that is, the summation of the refractive optical power (30 Diopters) and the diffractive optical power of the first diffraction order of multifocal phase plate 112 (+4 Diopters). The additional optical power of +4 Diopters provided by the multifocal phase plate 112 is referred to herein as the "add power" of the multifocal phase plate 112.

There are at least two potential benefits of an ophthalmic lens 100 as described in the previous paragraph. First, the add power produced by the first diffraction order of the multifocal phase plate 112 is such that the location of the first focus F1 and the second focus F2 along the optical axis 108 may be configured to provide both near vision and distant vision. That is, the first focus F1 is configured to provide distant vision, while the add power of the multifocal phase plate 112 is configured such that the second focus F2 provides near vision. Alternatively, the add power may be such that the first focus F1 provides distant vision, while the second focus F2 provides intermediate vision, for instance where the ophthalmic lens 100 is part of an accommodation lens system in which some accommodation is provided by a movement assembly that is responsive to the capsular bag and/or the ciliary muscles of the eye.

A second potential benefit of the above configuration is related to the chromatic dispersion produced by the first diffraction order of the multifocal and monofocal phase plates 112, 122. It is known in the art that chromatic dispersion of a first diffraction order is usually opposite in sign from the chromatic dispersion of typical refractive materials. The amount of negative dispersion resulting when the diffractive optical power is in the range of about +2 Diopters to about +4 Diopters is also approximately the amount of dispersion needed to offset the positive dispersion present in many optical materials, such as silicone or acrylic. Thus, the combination of a refractive lens with an optical power of about 20 to 40 Diopters with, for example, a multifocal phase plate having an add power of about +2 to +4 Diopters produces an optical element with reduced overall chromatic aberrations, since the refractive chromatic dispersion and diffractive chromatic dispersion approximately cancel one another.

Alternatively, the diffractive optical power of the phase plates 112, 122 may be outside the above range of about +2 Diopters to about +4 Diopters. The selected value of the diffractive optical power can depend on such parameters as the refractive optical power of the phase plates 112, 122, the total optical power of the ophthalmic lens 100, and the desired interaction between the diffractive and refractive components of the ophthalmic lens 100. The diffractive optical power of one or both of the phase plates 112, 122 may also be a negative Diopter power. The phase plates 112, 122 may otherwise be configured to adjust the chromatic aberrations of one or more of the first focus F1, the second focus F2, and the third focus F3. Also, the phase plates 112, 122 may be configured to adjust other monochromatic aberrations of one or more of the first focus F1, the second focus F2, and the third focus F3 (e.g., spherical aberrations, astigmatism, etc.).

In certain embodiments, the multifocal phase plate 112 may be a bifocal phase plate in which light incident upon the multifocal phase plate 112 is split primarily between two different diffraction orders, for example between the zeroth and first diffraction orders or between the first and second diffraction orders. The first region 110 and the multifocal phase plate 112 may be disposed such that light in the two diffraction orders are used to provide, for example, distant and near vision or distant and intermediate vision. In such embodiments, some light is usually also contained in other diffraction orders. The multifocal phase plate 112 may be configured to provide a significant amount of light in three or more diffraction orders. For example the multifocal phase plate 112 could provide three diffraction orders to provide near, intermediate, and distant vision or to provide an effectively increased depth of field.

In the illustrated embodiment shown in FIG. 3, the multifocal phase plate 112 is a MOD 1.5 phase plate and the monofocal phase plate 122 is a MOD 1 phase plate; however, other combinations of MOD x.5 and/or MOD y phase plates for the phase plates 112, 122 are consistent with embodiments of the present invention. The multifocal and monofocal phase plates 112, 122 may be configured such that the first focus F1 and third focus F3 are disposed at the same or substantially the same location. As used herein the term "substantially the same location," when used in reference to two or more foci of an optic or IOL according to embodiments of the invention, means (1) that the locations of the foci formed by light from two portions of an optic or IOL according to embodiments of the invention differ by no more that the depth of field or depth of focus of the portions, either individually or taken together, or (2) that the locations of the foci formed by light from two portions of an optic or IOL according to embodiments of the invention differ by an amount that is too small to be clinically significant (e.g., that difference in the locations of the two foci formed by the two portions of the optic or IOL is so small that an average patient would not detect a difference in the vision between a traditional IOL having a focal length equal to that of the first portion and a traditional IOL having a focal length equal to that of the second portion).

The multifocal phase plate 112 may be configured to produce a first diffraction order and a second diffraction order that each contain approximately 40% of the incident energy on the optic. The multifocal phase plate 112 and the base curvature C1 may be selected such that the first diffraction order corresponds to the first focus F1 and provides distant vision, while the second diffraction order corresponds to the second focus F2 and provides either near or intermediate vision. In addition, the MOD 1 phase plate 122, which provides primarily a first diffraction order only, may be configured to also provide distant vision.

The outer diameter D of the multifocal phase plate 112 may be selected to be approximately the same dimension as the pupil of the eye when under moderate to bright lighting conditions, such that little or no light is received by the second region 120 and the monofocal phase plate 122. Thus, most of the light received by the eye is received by the first region 110 and the multifocal phase plate 112, which provides both near vision and distant vision in approximately equal proportions. Under lower light conditions, such a normal room light or dim lighting, the iris of the eye normally dilates to a larger diameter so that more light enters the second region 120 and the MOD 1 phase plate 122. Thus, under lower lighting conditions, more light is directed to distant vision as the iris dilates, since all the light entering the monofocal phase plate 122 goes to providing distant vision. Therefore, the ophthalmic lens 100 favorably provides better distant vision under lower lighting conditions by directing a higher percentage of the available light to the distant vision. Such a lens is sometimes referred to as a "distant dominant lens."

Figure 4:
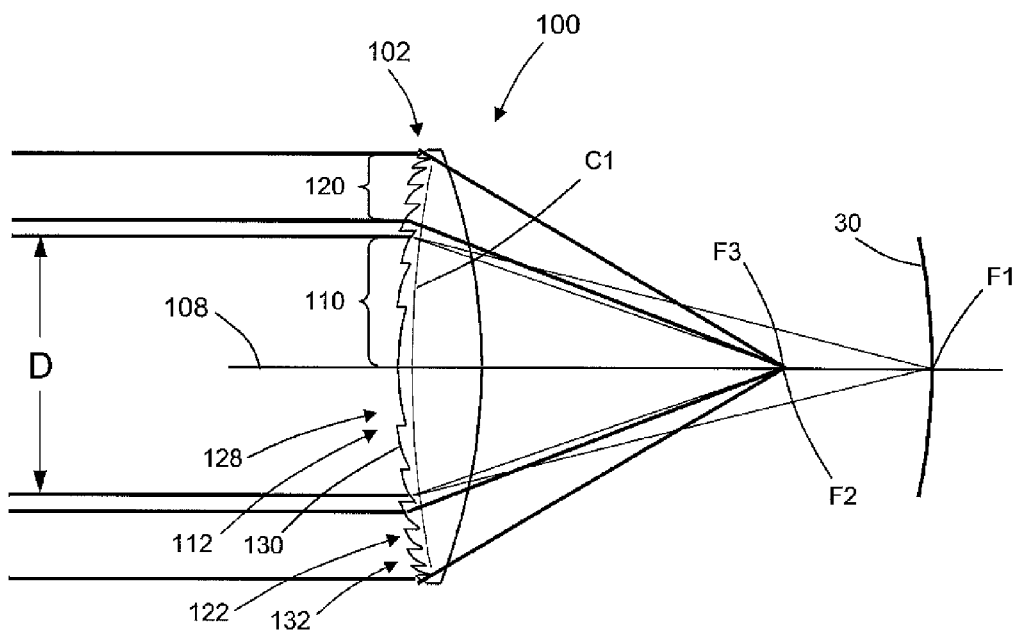
FIG. 4 is a side view of a second embodiment of a diffractive ophthalmic lens comprising a plurality of diffractive phase plates, wherein a peripheral phase plate is configured to provide near or intermediate vision.

In other embodiments, as illustrated in FIG. 4 for instance, the multifocal phase plate 112 is a MOD 1.5 phase plate and the monofocal phase plate 122 is a MOD 2 phase plate. In such embodiments, the first focus F1 provides distant vision and the second focus F2 provides near or intermediate vision, while the monofocal phase plate 122 produces the third focus F3, which may provide either near or intermediate vision. Thus, the ophthalmic lens 100 is configured such that the second focus F2 and third focus F3 are disposed at substantially the same location.

If the outer diameter D of the multifocal phase plate 112 is again selected to be approximately the same dimension as the pupil of the eye under bright lighting conditions, little or no light is received by the second region 120 and the monofocal phase plate 122 under such lighting conditions. However, in this configuration, as the iris of the eye dilates to a larger diameter, more light is directed to near or intermediate vision as the iris dilates, since all the light entering the MOD 2, monofocal phase plate 122 goes to providing near or intermediate vision. In this embodiment, therefore, the ophthalmic lens 100 provides better near or intermediate vision under lower lighting conditions and is referred to as a "near dominant lens."

Figure 5:
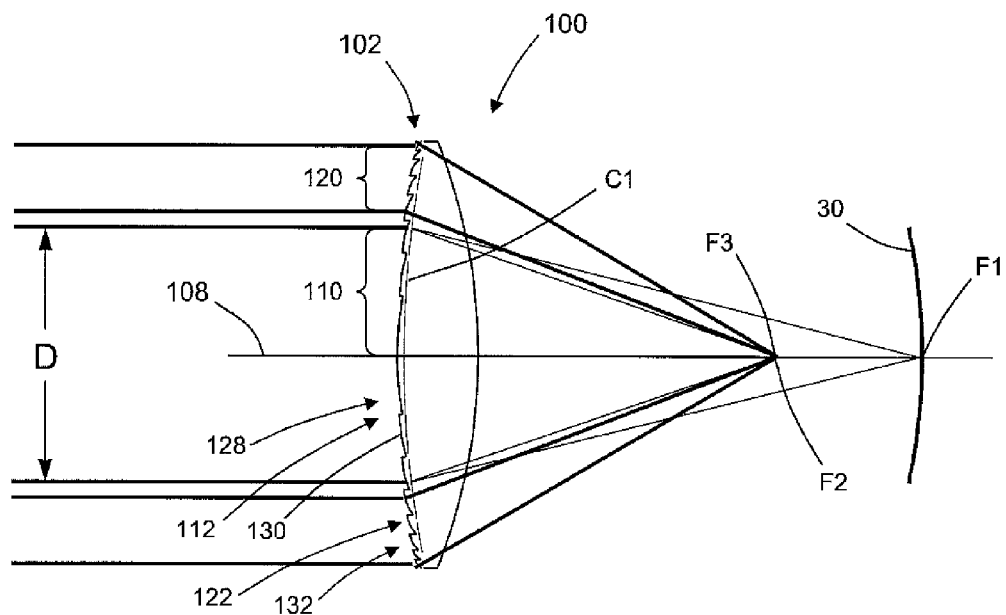
FIG. 5 is a side view of a third embodiment of a diffractive ophthalmic lens comprising a plurality of diffractive phase plates producing primarily two diffraction orders, wherein a peripheral phase plate is configured to provide near or intermediate vision.

Referring to FIG. 5, in some embodiments, the multifocal phase plate 112 of the ophthalmic lens 100 is a MOD 0.5 phase plate and the monofocal phase plate 122 is a MOD 1 phase plate. In such embodiments, the phase plates 112, 122 may both be disposed on the single base curvature C1. The MOD 0.5 phase plate 112 usually produces a zeroth diffraction order and first diffraction order which may be configured to correspond to distance vision and near or intermediate vision, respectively. The MOD 1 phase plate 122 also provides near or intermediate vision and has a single, first diffraction order which corresponds to the second focus F2. Thus, the second focus F2 produced by the MOD 0.5 phase plate 112 and third focus F3 produced by the MOD 1 phase plate are disposed at substantially the same location.

Preferably, the zeroth and first diffraction orders of the MOD 0.5 phase plate 112 are configured so that each diffraction order contains approximately 40% of the incident energy received by the optic 102, although other percentages for the two diffraction orders are also possible. Preferably, the ophthalmic lens 100 is configured to favorably provide a reduction in chromatic aberrations for near or intermediate vision, by selecting the phase plates 112, 122 so that the first diffraction orders of both phase plates 112, 122 produce negative dispersion that balances the positive dispersion produced by the refractive power of the first and second regions 110, 120.

As illustrated in FIG. 5, the ophthalmic lens 100 is a near dominant lens, since more of the MOD 1 phase plate 122 is exposed as the pupil of the eye in which the ophthalmic lens 100 is used dilates under lower lighting conditions. In certain instances, however, it may be preferred that the ophthalmic lens 100 be a distant dominant lens. One way of accomplishing this objective is to eliminate the monofocal phase plate 122 altogether, so that the second region 120 has only a refractive optical power, as discussed in greater detail below herein. One potential problem with this approach is the loss of the favorable chromatic aberration reduction provided by the negative dispersion of the monofocal phase plate 122.

Figure 6:
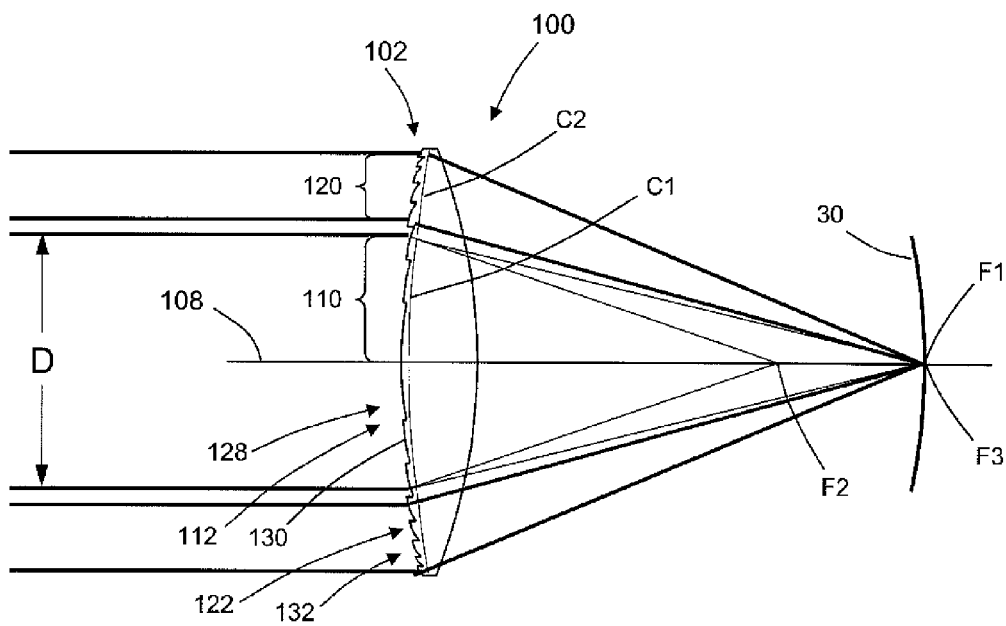
FIG. 6 is a side view of a fourth embodiment of a diffractive ophthalmic lens comprising a plurality of diffractive phase plates producing primarily two diffraction orders, wherein a peripheral phase plate is configured to provide distant vision.

An innovative way has been developed for overcoming this potential problem in which the ophthalmic lens 100 is simultaneously a distant dominant lens and able to provide reduced chromatic aberrations. Referring to FIG. 6, in certain embodiments, the ophthalmic lens 100 comprises the optic 102, the first region 110, and the second region 120, wherein the first region 110 comprises a multifocal phase plate 112 disposed on a first base curvature C1 that may have a first radius of curvature R1 (not shown) and the second region 120 comprises a monofocal phase plate disposed on a second base curvature C2 that may have a second radius of curvature R2 (not shown), the radius of curvatures R1, R2 being generally finite (i.e., are not flat or substantially flat, that is with surface deviations on the order of a wavelength of light or less). In such embodiments, the first radius of curvature R1 is different from the second radius of curvature R2. The first region 110 and second region 120 each have a refractive optical power that is produced by the finite radius of curvatures R1, R2, respectively.

The multifocal phase plate 112 may be configured to provide, produce, or form the first focus or focal point F1 and the second focus or focal point F2, where the location of the foci F1, F2 may be affected by the refractive optical power of the regions 110. For example, the second base curvature C2 may be configured such that the first focus F1 and third focus F3 are disposed at substantially the same location so as to provide distant vision, rather than near or intermediate vision, as in embodiments of the ophthalmic lens 100 illustrated in FIG. 5. One unexpected result of the present embodiment is that at least some reduction in chromatic aberrations may be provided both for distant vision and for near or intermediate vision, since the first diffraction order of the MOD 0.5 phase plate 112 reduces chromatic aberrations for near or intermediate vision, while the first diffraction order of the MOD 1 phase plate 122 is now configured to reduce chromatic aberrations for distant vision.

In certain embodiments, the base curvatures C1, C2 are spherical or substantially spherical in shape, while in other embodiments, one or more of the base curvatures C1, C2 may be aspheric and/or asymmetric in shape (e.g., have a surface shape that is other than a spherical shape). As used herein, the term "substantially spherical" means that deviations in the shape of a surface from that of a spherical surface are less than at least about 10 wavelengths of visible light, preferably less than 5 wavelengths of visible light, and even more preferably less than 1 wavelengths of visible light. It will be understood by those of skill in the art that an aspheric surface is generally characterized by a radius of curvature (e.g. the R1, R2), wherein the shape of at least a portion of the aspheric surface deviates from that of a sphere having the characteristic radius of curvature. In such embodiments, the aspheric base curvature may be characterized by the radii R1, R2, respectively. For example, one or both of the base curvatures may be defined by an aspheric equation such as Equation (3) in which R1 and/or R2 represent a central lens radius of the corresponding base curvature.

Figure 7:
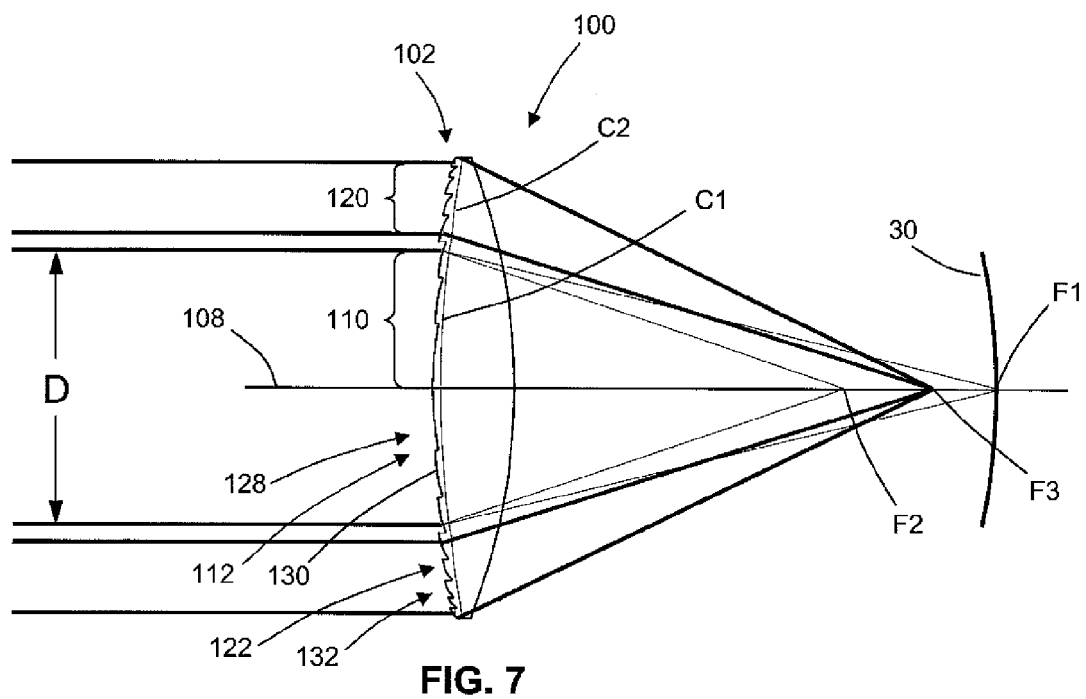
FIG. 7 is a side view of a fifth embodiment of a diffractive ophthalmic lens comprising a plurality of diffractive phase plates producing primarily two diffraction orders, wherein the peripheral phase plate is configured to provide a focus or focal point that is disposed between the foci produced by the central phase plate.

In certain other embodiments, as illustrated in FIG. 7, the MOD 1 phase plate 122 and radius of curvature R2 of the second base curvature C2 may be configured independently of the first region 110 parameters such that the third focus F3 produced by the second region 120 is located on neither the first focus F1 nor the second focus F2 produced by the first region 110. For example, the second base curvature C2 may be configured such that the third focus F3 is disposed along the optical axis between the first focus F1 and the second focus F2. In such embodiments, the first focus F1 may provide distant vision, while the second focus F2 may provide near vision and the third focus F3 may provide intermediate vision. Alternatively, the MOD 1 phase plate 122 and the second base curvature C2 could be configured to locate the third focus F3 at any preferred location either on optical axis 108 or some distance off the optical axis 108, for instance, to accommodate macular degeneration. In general, the parameters defining the phase plate 122 and the second base curvature C2 may be selected to provide a focus that is completely independent of the first and second foci F1, F2 in terms of location, chromatic aberrations, or other focus parameters or characteristics. For example, the second region 120 of the ophthalmic lens 100 may be configured so that most of the light diffracted by the phase plate 122 is contained in a −1 diffraction order, which provides, among other things, a positive amount of chromatic dispersion.

In still other embodiments, the multifocal phase plate 112 is a MOD x.5 phase plate and monofocal phase plate 122 is a MOD y phase plate, where x and y are integers, as explained above herein. For example, x may be greater than or equal to 2 such that the $x^{th}$ diffraction order corresponds to the first focus F1 and provides distant vision, and the $(x+1)^{th}$ diffraction order corresponds to the second focus F2 and provides near or intermediate vision. The monofocal phase plate 122 may be configured so that most of the diffractive optical power corresponds to either the first focus F1 (e.g., y=x) or second focus F2 (e.g., y=x+1), depending on whether the ophthalmic lens 100 is to be distant dominant lens or near dominant lens, respectively. Alternatively, the ophthalmic lens 100 may be configured so that most of the light diffracted by at least one of the phase plates 112, 122 is contained in a −1 diffraction order.

In addition to the various parameters and preferred ranged outlined above herein, embodiments of the ophthalmic lens 100 advantageously provide a lens designer with additional independent parameters, such as the independent choice of the radius of curvatures R1, R2 of the first and second base curvatures C1, C2, respectively. In some embodiments, the step height between the diffraction zones 130 of the one of the phase plates 112, 122 is selected based on a design wavelength that is different from the design wavelength selected for the other phase plate 112, 122. For example, the step height between diffractive zones or echelettes 130 for the monofocal phase plate 122 may be selected based on a design wavelength that is shifted toward a bluer wavelength as compared to the design wavelength for the multifocal phase plate 112. The selection of a blue shifted design wavelength for the monofocal phase plate 122 may for example, advantageously provide better scotopic vision due to the eyes greater sensitivity to light in blue wavelength band. In general, a design parameter or configuration discussed with regard to one embodiment of the ophthalmic lens 100 illustrated in one of the figures is also available for embodiments of the ophthalmic lens 100 illustrated in the other figures.

Figure 8:
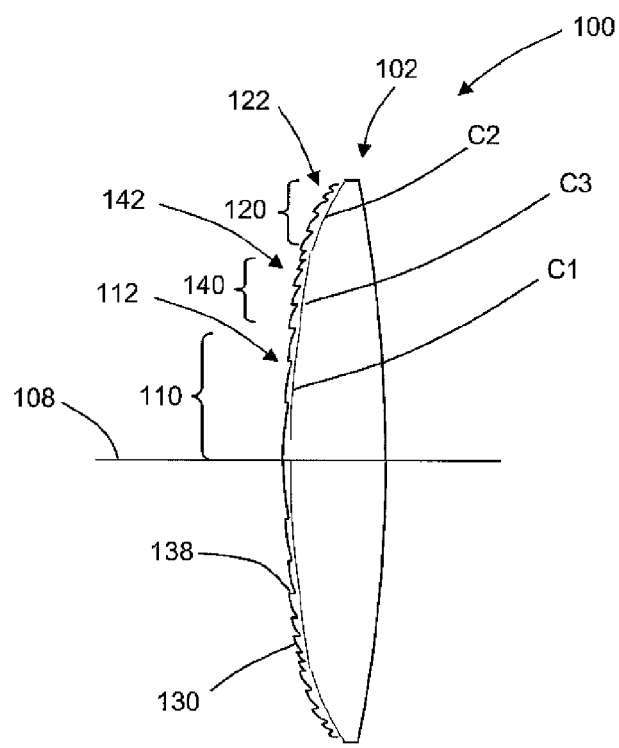
FIG. 8 is a side view of a sixth embodiment of a diffractive ophthalmic lens comprising three diffractive phase plates.

Referring to FIG. 8, the ophthalmic lens 100 may further comprise a third region 140 having a refractive optical power, where the third region 140 comprises a third phase plate 142. The third phase plate 142 may, for example be a multifocal phase plate or a monofocal phase plate. In such embodiments, the third region 140 may be disposed between the first region 110 and the second region 120, as illustrated in FIG. 8. Alternatively, the third region 140 may be disposed outside the first region 110 and the second region 120. The third region 140 may further comprise a third base curvature C3 having a radius of curvature R3, where the third base curvature C3 is either different from the base curvatures C1, C2 of the first and second regions 110, 120 or, alternatively, be substantially the same as at least one of the base curvatures C1, C2 (e.g., having the same radius of curvature as the base curvature C1). In certain embodiments, the base curvatures C1, C2, C3 are spherical or substantially spherical in shape, while in other embodiments, one or more of the base curvatures C1, C2, or C3 may be aspheric and/or asymmetric in shape.

In certain embodiments, the third region 140 may be an intermediate region disposed between the first region 110 and the second region 120 so that the third phase plate 142 is disposed between the multifocal and monofocal phase plates 112, 122. In such embodiments, the intermediate phase plate 142 may be configured to provide a transition between multifocal phase plate 112 and the monofocal phase plate 122. For example, the diffraction zones 130 of the intermediate phase plate 142 may be configured to have steps 138 with a step size that is between those of the multifocal and monofocal phase plates 112, 122. In one embodiment, the step height between the diffraction zones 130 of the intermediate phase plate 142 are constant and is selected based on a design wavelength that is different from the design wavelength selected for the multifocal phase plate 112 and the monofocal phase plate 122. Such a selection may be used advantageously to blur the edges of a halo formed by a bifocal or multifocal lens. In other embodiments, the step height between the diffraction zones 130 of the intermediate phase plate 142 varies over the third region 140, for example, as a function of radius.

For any of the embodiments of the ophthalmic lens 100 discussed herein, the multifocal phase plate 112 and the monofocal phase plate 122 may be disposed in a manner that best suits a particular application or design. For instance, the monofocal phase plate 122 may be disposed in the center of the ophthalmic lens 100 and the multifocal phase plate 112 outside the monofocal phase plate 122. Alternatively, both phase plates 112, 122 may have annular shapes such that neither is disposed in the center of the ophthalmic lens 100. For example, the center of the ophthalmic lens 100 may be a void, a refractive optical element, or some other type of optical element about which the phase plates 112, 122 are disposed.

Figure 9:
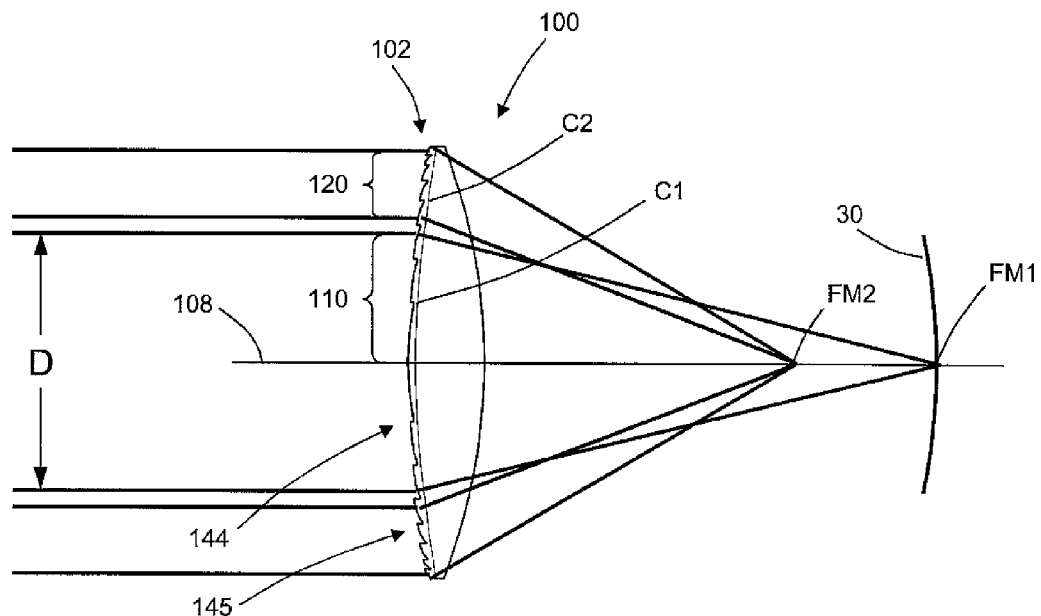
FIG. 9 is a side view of a eighth embodiment of a diffractive ophthalmic lens comprising two phase plates, each phase plate disposed on a different, finite radius of curvature.

Referring to FIG. 9, in certain embodiments, the first region 110 of the ophthalmic lens 100 comprises a first monofocal phase plate 144 disposed on the first base curvature C1 and the second region 120 of the ophthalmic lens 100 comprises a second monofocal phase plate 145 disposed on the second base curvature C2. The optical power of the first base curvature C1 may be greater than the optical power of the first monofocal phase plate 144 and the optical power of the second base curvature C2 may be greater than the optical power of the second monofocal phase plate 145. Preferably, the first base curvature C1 has a finite first radius of curvature R1 that is different from a finite second radius of curvature R2 of the second base curvature C2. In this way, the first radius of curvature R1 and the second radius of curvature R2 are independent design parameters that may be advantageously selected to be compatible with the first and second monofocal phase plates 144, 145 in providing two or more foci.

The first monofocal phase plate 144 may be configured to produce a chromatically corrected first focus FM1 providing distant vision and the second monofocal phase plate 145 may be configured to provide a chromatically corrected second focus FM2 providing near or intermediate vision. This would advantageously provide a patient with both good distant vision under bright outdoor lighting conditions, where the pupil is relatively small, and better near or intermediate vision under dimmer indoor lighting conditions, where the pupil dilates to uncover more of the second monofocal phase plate 145.

It will be appreciated that the phase plates 144, 145 typically have a high amount of chromatic dispersion as compared to a refractive element having a similar amount of optical power. As discussed above herein, the chromatic dispersion of the phase plates 144, 145 are also generally opposite in sign to the chromatic dispersion of a refractive element. As a result, the first and second monofocal phase plates 144, 145 may be advantageously configured to have relatively low optical powers, such that their chromatic dispersion due to diffraction is approximately the same magnitude, but opposite sign, as the chromatic dispersion of the first and second base curvatures C1, C2, which have relatively high optical powers. Therefore, the resultant chromatic aberrations may be substantially reduced for the combinations of the first monofocal phase plate 144 with the first base curvature C1 and second monofocal phase plate 145 with the second base curvature C2.

In other embodiments, the phase plates 144, 145 may both be multifocal phase plates or bifocal phase plates. In yet other embodiments, the ophthalmic lens 100 may be configured so that most of the light diffracted by at least one of the phase plates 144, 145 is contained in a higher or lower diffraction order (e.g., a diffraction order other than the zeroth or first diffraction order). It will be appreciated that the various design parameters available for embodiments of the ophthalmic lens 100 illustrated in any one of FIGS. 3-9 may, when appropriate, also be available in the other embodiments of ophthalmic lens 100 discussed herein.

Figure 10:
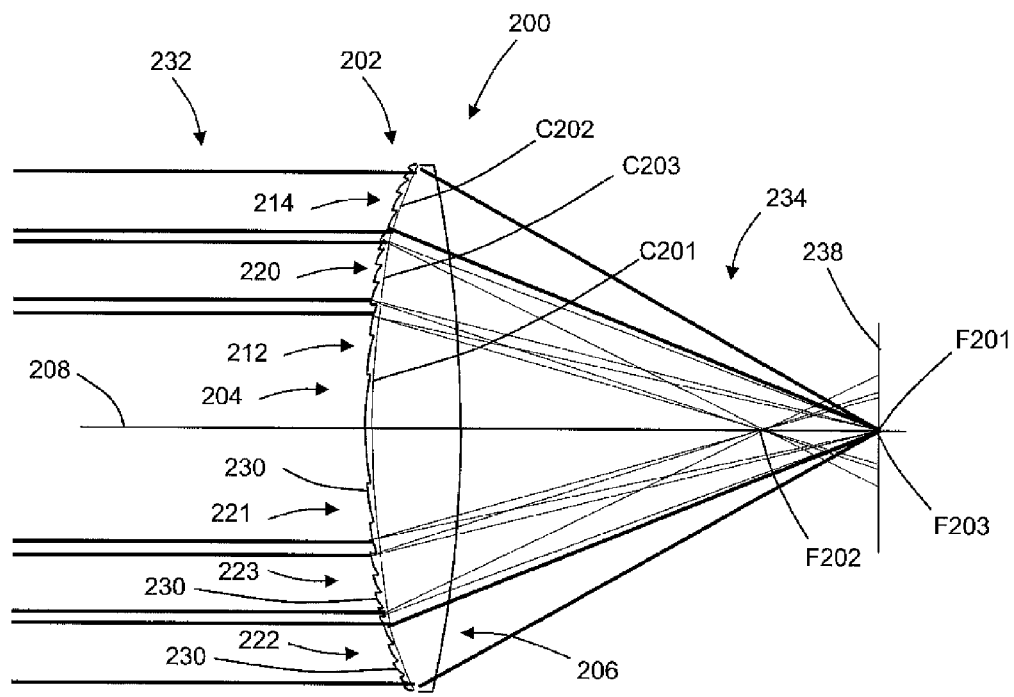
FIG. 10 is a side view of the ninth embodiment of a diffractive ophthalmic lens comprising an intermediate phase plate disposed between a bifocal phase plate and a monofocal phase plate.

Referring to FIG. 10, in certain embodiments, an ophthalmic lens 200 comprises an optic 202 having an anterior surface 204, a posterior surface 206, and an optical axis 208. The ophthalmic lens 200 further comprises a multifocal phase plate 212 configured to direct light to a first focus F201 and a second focus F202, a monofocal phase plate 214 configured to direct light to a third focus F203, and an intermediate or transition phase plate 220 located between the multifocal phase plate 212 and the monofocal phase plate 214. The multifocal phase plate 212 comprises a first plurality 221 of echelettes 230 disposed on a first base curvature C201 having a first radius of curvature R201 and monofocal phase plate 214 comprises a second plurality 222 of echelettes 230 disposed on a second base curvature C202 having a second radius of curvature R202 that is preferably different from the first radius of curvature R201. The intermediate phase plate 220 comprises a third plurality 223 of echelettes 230 configured to change the overall resultant amplitude and/or distribution of light directed to the first focus F201 and/or the second focus F202. The third plurality 223 of echelettes 230 are disposed on a third base curvature C203 having a third radius of curvature R203.

It will be appreciated that the various design parameters available for embodiments of the ophthalmic lens 100 illustrated in anyone of FIGS. 3-9 may, when appropriate, also be incorporated into embodiments of ophthalmic lens 200. For example, in contrast to the embodiments illustrated in FIG. 10, the multifocal phase plate 212 may be disposed at the periphery of the optic 202 and the monofocal phase plate 214 may be disposed at or near the center of the optic 202. Additionally, the phase plates 212, 214 may alternatively be disposed on the posterior surface 206 rather than the anterior surface 204. In other embodiments, the phase plates 122 and the plates 212, 214 may be disposed on opposite surfaces of the optic 202. In addition, any of the materials and geometries discussed regarding the ophthalmic lens 100 may also be incorporated into the ophthalmic lens 200.

Referring again to the illustrated embodiment shown in FIG. 10, a set of incident rays 232, for example from a distant point source, are incident on the phase plates 212, 214, 220 of the ophthalmic lens 200. The use of rays during the following discussion is illustrative only and is meant to point out certain inventive aspects of the ophthalmic lens 200. The incident rays 232 interact with the ophthalmic lens 200 to produce corresponding focused rays 234. More specifically, the rays 232 incident on the monofocal phase plate 214 produce focused rays 234 that are directed to the third focus F203, as illustrated by the heavier weight lines in FIG. 10 representing the focused rays 234. The rays 232 incident on the multifocal phase plate 212 and the intermediate phase plate 220 produce focused rays 234 that are split between the first and second foci F201, F202, as illustrated by the lighter weight lines in FIG. 10 representing the focused rays 234. In the illustrated embodiment, first and third foci F201, F203 are disposed at substantially the same location. In certain embodiments, the first focus F201 and/or the third focus F203 may be disposed to provide distant vision and the second focus F202 may be disposed to provide near or intermediate vision. It will be appreciated by one of normal skill in the art that the magnitude of the rays or the amount of light directed to the first and second foci F201, F202 by the phase plates 212, 220 depends, at least in part, upon the step between adjacent echelettes 230 of the phase plates 212, 220. The focused rays 234 focusing onto the second focus F202 continue to propagate to form an out-of-focus image on an image plane 238 passing through the first and/or third foci F201, F203. This out-of-focus image is referred to herein as "halo image", consistent with the common usage of this term within the art. The image plane 238 may be flat, as shown in FIG. 1, or have a more general shape such as a spheroid, for example, as in the case where the ophthalmic lens 200 is implanted into an eye as an IOL, wherein the image plane 238 is the retina of the eye.

Figure 11:
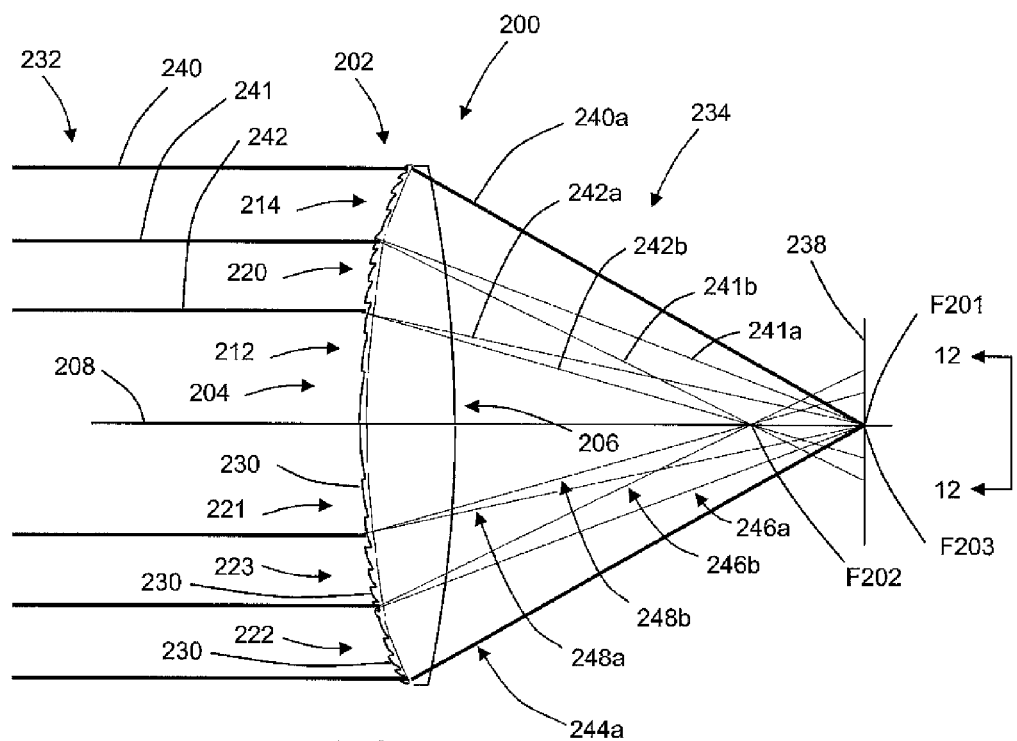
FIG. 11 is the diffractive ophthalmic lens shown in FIG. 10 showing incident ray impinging the outer peripheries of the intermediate phase plate, bifocal phase plate, and monofocal phase plate.

Referring to FIG. 11, the ophthalmic lens 200 shown in FIG. 10 is illustrated with a selected number of the incident rays 232 and focused rays 234 in order to illustrate certain inventive aspects of the ophthalmic lens 200. Specifically, an incident ray 240 incident just within the outer periphery of the monofocal phase plate 214 is directed to the third focus F203 as focused ray 240a. In addition, an incident ray 241 incident inside the outer periphery of the intermediate phase plate 220 is schematically split into two rays, a focused ray 241a directed to the first focus F201 and focused ray 241b directed to the second focus F202. Similarly, an incident ray 242 incident inside the outer periphery of the multifocal phase plate 212 is schematically split into two rays, a focused ray 242a directed to the first focus F201 and focused ray 242b directed to the second focus F202. As will be appreciated, the rays 240a, 241a,b and 242a,b are representative of various loci of rays produced by the multifocal phase plate 212, the intermediate phase plate 220, and the monofocal phase plate 214. For example, the focused ray 240a belongs to a locus of rays 244a corresponding to all rays incident just within the outer periphery of the intermediate phase plate 220 that are then directed to the first focus F201. Similarly, the focused rays 241a, 241b, 242a, and 242b belong to loci of rays 246a, 246b, 248a, and 248b, respectively.

Figure 12:
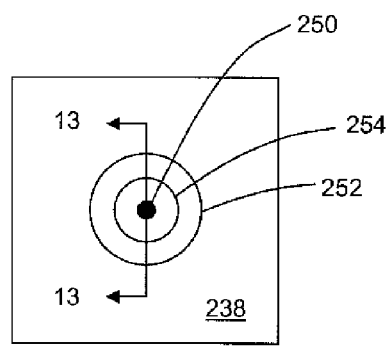
FIG. 12 is a front view of an image plane disposed at one of the focuses produced by the diffractive ophthalmic lens illustrated in FIG. 10.

Referring to FIG. 12, a front view of the image plane 238 of FIG. 11 is shown illustrating the intersection of the loci of rays 242a, 244a, 244b, 246a, 246b with the image plane 238. A filled circle 250 represents the intersection of the image plane 238 with the loci of rays 244a, 246a, and 248a, since light form these rays are focused onto the image plane 238. Circles 252 and 254 represent the intersection of the image plane 238 with the loci of rays 246b and 248b, respectively. Light contained within the circles 252, 254 (apart from that contained in the filled circle 250) contributes to the formation of a halo image of the type commonly associated with multifocal ophthalmic lenses. Upon inspection of FIGS. 11 and 12, it will be appreciated that, in certain embodiments, light incident upon the intermediate phase plate 220 will be substantially located between the circles 252, 254, while light incident upon the multifocal phase plate 212 will be substantially located inside the circle 254. This will be true to the extent that light incident upon the phase plates 212, 220 acts in accordance to the geometric optical representations illustrated in FIGS. 11 and 12. That is, when a fall physical optics representation of the ophthalmic lens 200 is used, it will be appreciated that some light will scattered outside the regions just stated. Similarly, it will be appreciated that some light will scattered outside the regions just stated when light from an extended source is used.

Embodiments of the present invention have resulted from the recognition that the shape of a halo image may have an effect on the perceived level of disturbance caused by such halos. In light of this recognition, it has been found that an intermediate phase plate such as the intermediate phase plate 220 may be advantageously configured to change the overall resultant amplitude and/or distribution of light directed to the second focus F202, thereby mitigating the level of disturbance generally associated with halo images. At least one method of accomplishing this benefit is to adjust the amount of energy going into, for example, zeroth and first diffraction orders by forming a phase plate having a grating step height $h_{step}$ that is different from that given by Equation 1 (i.e., a $\lambda/2$ phase plate). In one embodiment, the multifocal phase plate 212 is a $\lambda/2$ phase plate, the monofocal phase plate 214 is a $1\lambda$ phase plate, and the intermediate phase plate 220 is configured such that, $$h_{step} = \frac{\lambda}{4(n_{IOL} - n_o)}, \quad (4)$$

herein referred to as a λ/4 phase plate. In such embodiments, about 10% of the available energy transmitted through the intermediate phase plate 220 goes into the first diffraction order and about 80% of the available energy goes into the zeroth diffraction order.

Figure 13:
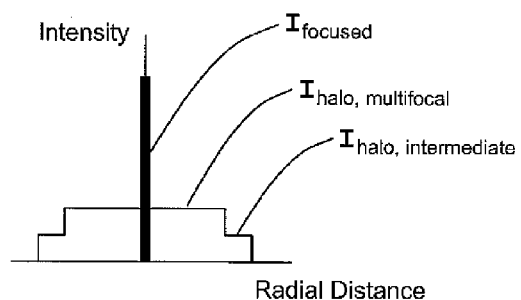
FIG. 13 is a graphical representation of intensity profiles along the cross-section 13-13 in FIG. 12.
Figure 14:
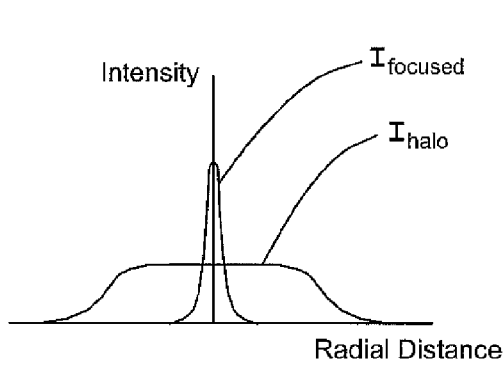
FIG. 14 is a graphical representation of the intensity distribution light along the cross-section 13-13 shown in FIG. 12 including physical optics effects.

Referring to FIGS. 13 and 14, potential benefits in configuring the intermediate phase plate 220 as, for example, a λ/4 phase plate will now be discussed. FIG. 13 is a graphical representation of intensity profiles along the cross-section 13-13 in FIG. 12 and is a plot of intensity verses distance from the optical axis 208. The intensity profiles shown may be obtained by plotting the intensity along the cross-section 13-13 of (1) focused light within the solid circle 250 produced by monofocal phases plate 214 and the zeroth diffraction orders of the phase plates 212, 220 ($I_{focused}$), (2) light contributing to the halo image contained within the circle 252 and produced by the first diffraction order of the intermediate phase plate 220 ($I_{halo, intermediate}$), and (3) light contributing to the halo image contained within the circle 254 and produced by the first diffraction order of the multifocal phase plate 220 ($I_{halo, multifocal}$). The plots in FIG. 13 are based on a geometric optics approximation in which light may be represented as rays, as illustrated in FIG. 11, for example.

Figure 15:
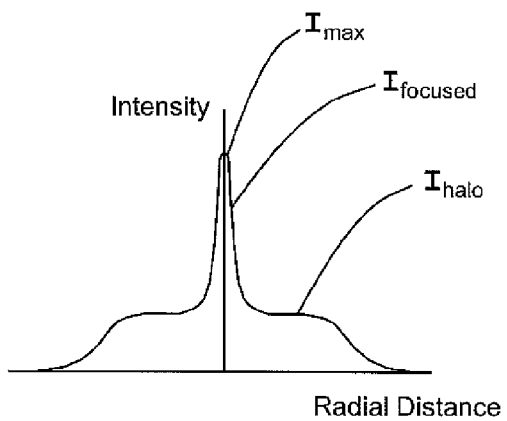
FIG. 15 is a graphical representation of the intensity distribution light along the cross-section 13-13 shown in FIG. 12 showing the summation of the various components illustrated in FIG. 14.
Figure 16:
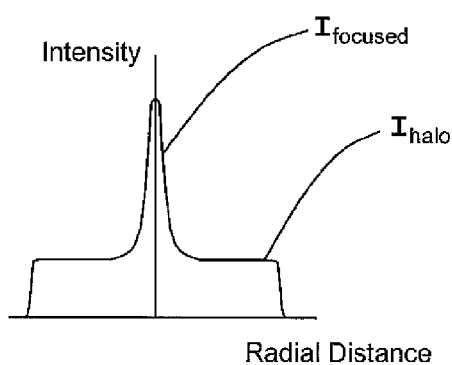
FIG. 16 is a graphical representation of the intensity distribution light for an ophthalmic lens not containing an intermediate phase plate.

FIG. 14 is a representation of intensity profiles resulting from light from a distant light source (either a point source or extended source) based on a physical optics treatment in which the diffractive effects of, for example, the finite apertures of the phase plates 212, 214, 220 are taken into account. The plot in FIG. 14 also takes into account the effects produced by an extended source and of dispersion resulting from a source containing light over a broad spectrum and not simply at the design wavelength λ. In these plots, $I_{halo}$ contains the combined effect of the first diffraction orders produced by the multifocal phase plate 212 and the intermediate phase plate 220 that contribute to the halo image. The addition of $I_{focused}$ and $I_{halo}$ is illustrated in FIG. 15, where $I_{focused}$ now represents the portion of the intensity plot dominated by zeroth diffraction order light and $I_{halo}$ represents the portion of the intensity plot dominated by first diffraction order light coming from the multifocal phase plate 212 and the intermediate phase plate 220. It will be appreciated that these plots are not necessarily to scale. For example, the maximum peak intensity $I_{max}$ is generally at least about an order of magnitude higher than the intensities found in the $I_{halo}$ portion of the plot. It will also be appreciated that peripheral portions of the plot $I_{halo}$ are significantly sloped. It has been found that halo images with this type of sloped-periphery intensity profile are generally less noticeable by a subject and may, therefore, be better tolerated than those produced, for example, by the profile illustrated in FIG. 16 in which there is a relatively sharp cut-off in the intensity at the periphery (some rounding of the peripheral portions of $I_{halo}$ are caused by physical optics and light dispersion effects). The profile illustrated in FIG. 16 has been found to be typical of ophthalmic lenses in which there is no intermediate phase plate (e.g., an IOL having multifocal phase plate across the entire optic region or an IOL in which (1) a central portion of the IOL comprises a bifocal λ/2 phase plate and (2) a peripheral portion comprises either a monofocal 1λ phase plate or simply a refractive zone with no diffractive phase plate).

Figure 17:
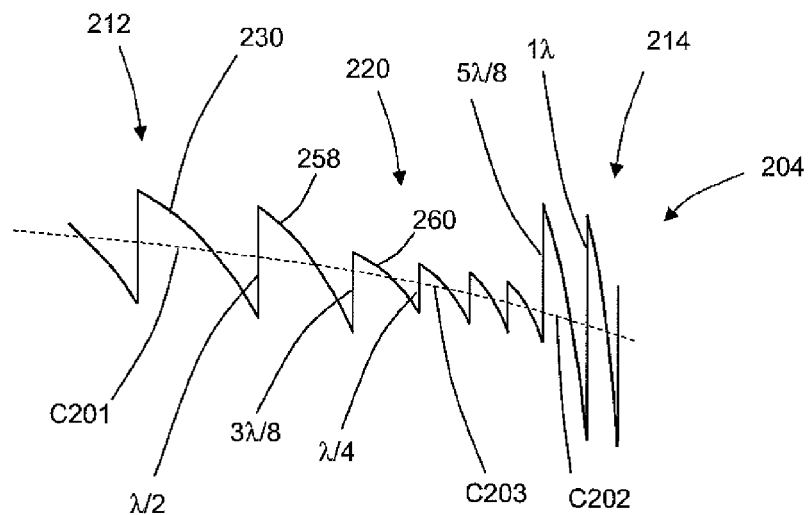
FIG. 17 is an embodiment of an ophthalmic lens according to the present invention illustrating the profile of the echelette in an intermediate phase plate, bifocal phase plate, and monofocal phase plate.

In certain embodiments, the intermediate zone plate 220 of the ophthalmic lens 200 comprises two or more echelettes 230 having the same height along the optical axis. For example, the number of echelettes 230 having the same height may be 3 echelettes to 5 or more echelettes, with a larger number of echelettes 230 being favored in cases where better diffractive performance is desired and a smaller number of echelettes 230 being favored in cases where a smaller outer diameter for the intermediate zone 220 is favored. Referring to FIG. 17, for example, the intermediate zone plate 220 may comprise 4 echelettes each having a phase step between echelettes 230 of λ/4. FIG. 17 also illustrates some of the echelettes 230 of the multifocal phase plate 212 and the monofocal phase plate 214 disposed near the intermediate zone plate 220. In the illustrated embodiment shown in FIG. 17, the echelettes 230 of the intermediate phase plate 220 are disposed on the base curvature C203 in such a way that they are centered about the base curvature C203 in a direction that is parallel to the optical axis 208 (see FIG. 11). In similar fashion, the echelettes 230 of the phase plates 212, 214 are disposed on the base curvatures C201, C202, respectively, such that they are centered about the base curvatures C201, C202 in a direction that is parallel to the optical axis 208. It has been found that this arrangement of the echelettes 230 of the phase plates 212, 214, 220 maintains a consistent phase relationship over the entire surface upon which the phase plates are placed (e.g., the anterior surface 204 illustrated in FIG. 17). These types of phase considerations are discussed by Cohen in U.S. Pat. No. 4,881,805. In certain embodiments, the desired phase relationship between the phase plates 212, 214, 220 is maintained by varying the step size between adjacent zone plates as indicated in FIG. 17. For example, the phase step height between adjacent echelettes 230, along with the phase height of the echelette along the optical axis 208, is λ/2 for the multifocal phase plate 212 and λ/4 for the intermediate phase plate 220. However, in order to maintain the desired phase relationship between phase plates, the phase step height between a last echelette 258 of the multifocal phase plate 212 and a first echelette 260 of the intermediate phase plate 220 is adjusted to 3λ/8. Similarly, as also illustrated in FIG. 17, a 5λ/8 phase step height is used between the intermediate phase plate 220 and the monofocal phase plate 214. By contrast, FIG. 1D of U.S. Pat. No. 5,699,142 centers the steps between echelettes on a base curve rather than centering the surface of the echelette itself about the base curve, as seen in FIG. 17 of the present embodiment.

In other embodiments, the intermediate phase plate 220 comprises 3, 4, 5 or more echelettes 230 having phase heights of 3λ/4 each. Such an arrangement of the echelettes 230 may be used to increase the amount of energy into the first diffraction order. This configuration may be used to increase the amount of energy in the second focus F202, thereby producing an intensity profile along the cross-section 13-13 in which the intensity at the peripheral edges is higher than the intensity profile closer to the optical axis 208. In general, any number of echelettes having any predetermined phase height between echelettes may be used to provide a predetermined distribution of energy between two or more diffraction orders and, therefore, a predetermined effect on the intensity profile produced by a halo.

In certain embodiments, such alterations to the intensity profile may be used to induce or cause the eye to favor a predetermined pupil diameter, for example, as discussed by Griffin in U.S. Pat. No. 6,474,814, herein incorporated by reference. Alternatively or additionally, the radius of curvature or some other parameter of the second base curvature C202 may be modified to redirect energy into the first focus F201 or some other focus, such as an intermediate focus disposed between the first focus F201 and the second focus F202.

In still other embodiments, the intermediate phase plate 220 comprises two echelettes 230 having one phase height disposed nearer the multifocal phase plate 212 and two echelettes 230 having a different phase height disposed nearer the monofocal phase plate 214. For example, the intermediate phase plate 220 may comprise two echelettes 230 having phase heights of $3\lambda/8$ located proximal the multifocal phase plate 212 and two echelettes 230 having phase heights of $\lambda/8$ located proximal the monofocal phase plate 214. Such staggering of the echelettes of the intermediate phase plate 220 may be used to further modify the slope of the peripheral edges of the intensity profile shown in FIGS. 14 and 15.

Figure 18:
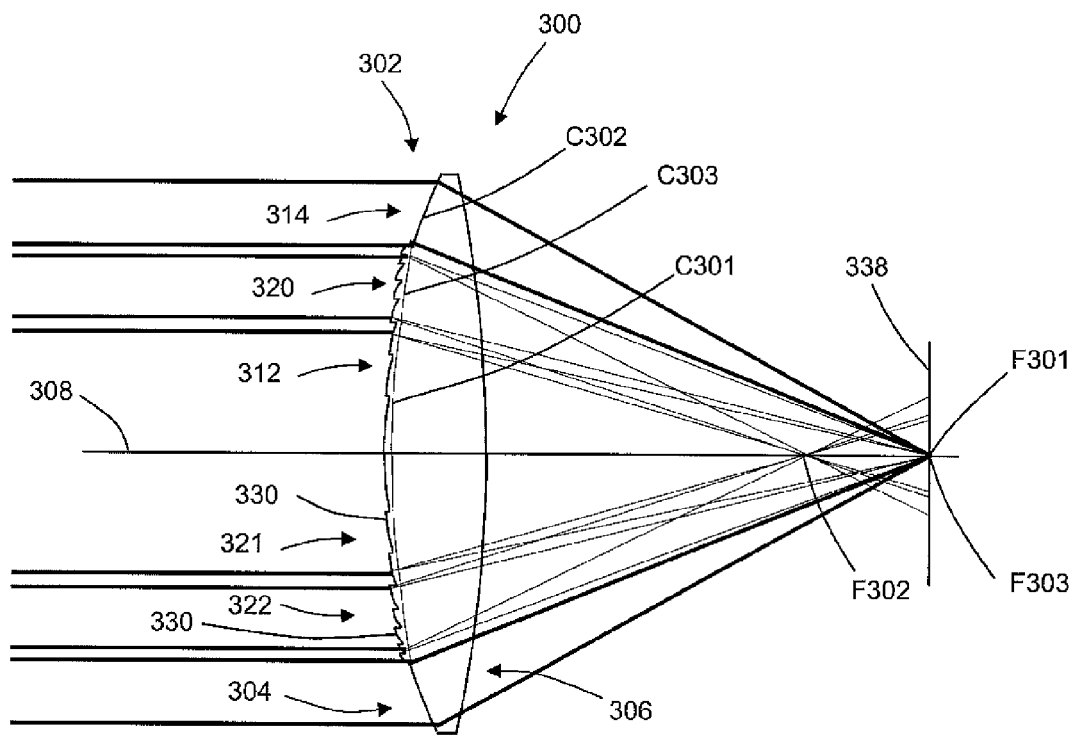
FIG. 18 is a side view of the tenth embodiment of a diffractive ophthalmic lens comprising an intermediate phase plate disposed between a bifocal phase plate and a refractive region.

Referring to FIG. 18, in certain embodiments, an ophthalmic lens 300 comprises an optic 302 having an anterior surface 304, a posterior surface 306, and an optical axis 308. The ophthalmic lens 300 further comprises a multifocal phase plate 312 configured to direct light to a first focus F301 and a second focus F302, an outer refractive region 314 having a refractive optical power and no diffractive optical power, and an intermediate phase plate 320 surrounding the inner phase plate 312 and configured to change the overall resultant amplitude and/or distribution of light directed to the second focus F302. The multifocal phase plate 312 comprises a first plurality 321 of echelettes 330 disposed about a first base curvature C301 that may have a radius of curvature R301 (not shown). The outer refractive region 314 surrounds the intermediate phase plate 320 and is configured to direct light to a third focus F303 and/or to the first focus F301. The intermediate phase plate 320 comprises a second plurality 322 of echelettes 330 disposed about the first base curvature C301 or about a second base curvature C302. It will be appreciated that the various design parameters available for embodiments of the ophthalmic lens 100 illustrated in anyone of FIGS. 3-17 may, when appropriate, also be incorporated into embodiments of ophthalmic lens 200.

In certain embodiments, the outer refractive region 314 may be configured to be disposed on a third base curvature C303 that is different from that of the first base curvature C301 of the multifocal phase plate 312. For example, outer refractive region 314 may be disposed on a third base curvature C303 having a radius of curvature selected to direct incident light to the second focus F302 rather than the first focus F301, for instance, in order to make the ophthalmic lens more near vision dominant when the pupil of the eye is larger. Alternatively, third base curvature C303 may have a radius of curvature the is configured to direct light to a focus F303 that is between the first and second foci F301, F302, or some other location on or off of the optical axis 308. Besides having a different radius of curvature, the outer refractive region 314 may alternatively or additionally be shaped differently from the shape of the base curvature C301. For example the outer refractive region 314 may have an aspheric shape configured to reduce an optical aberration, such as a spherical aberration. Alternatively, the outer refractive region 314 may be configured to be a multifocal or bifocal lens having more than one radius of curvature.

Figure 19:
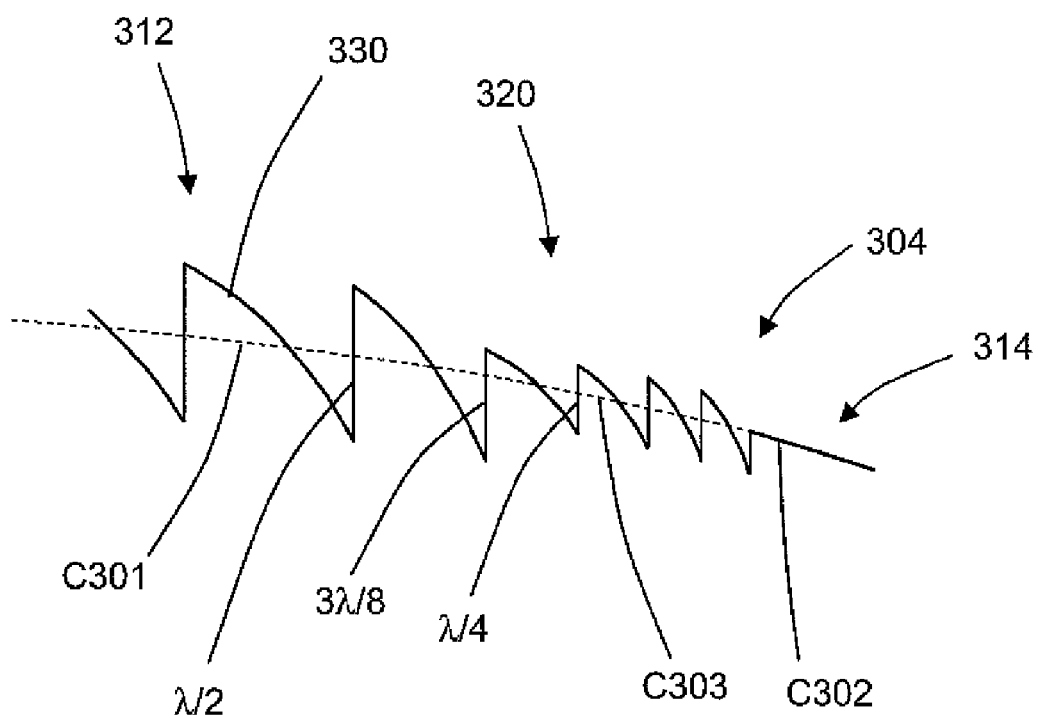
FIG. 19 is an embodiment of an ophthalmic lens according to the present invention illustrating the profile of the echelette in an intermediate phase plate, bifocal phase plate, and refractive region.

In certain embodiments, the echelettes 330 of the intermediate phase plate 320 are configured to have a zeroth diffraction order that directs some incident light to the first focus F301 and a first diffraction order that directs some incident light to the second focus F302. Referring to FIG. 19, the intermediate phase plate 320 may be configured with a plurality of echelettes 330 (for example, the four echelettes of the illustrated embodiment) having a phase height of $\lambda/4$, so that only about 10% of light incident on the intermediate phase plate 320 is directed to the second focus F302. In such embodiments, the reduced amount of light directed to the second focus F302 results in a halo image about the first focus F301 that has peripheral edges that are significantly sloped, thus reducing the disturbance to a subject seeing the halo image. It will be appreciated that the configurations of the intermediate phase plate 220 of the ophthalmic lens 200 discussed above may also be advantageously applied here, with similar results, to the intermediate phase plate 320.

In other embodiments, the second plurality 322 of echelettes 330 forming the intermediate phase plate 320 may be centered about a third base curvature C303 having a radius of curvature different from that of the base curvature C301 or having some other characteristic different from that of the base curvature C301. For example, the radius of curvature of the third base curvature C303 may be configured to be larger than that of the first base curvature C301, such that light in the first diffraction order of the intermediate phase plate 320 is directed toward the first focus F301 instead of second focus F302. Alternatively, the base curvature of the intermediate phase plate 320 may configured with a radius of curvature that is selected to direct light to a focus between the first and second foci F301, F302 or to be otherwise configured to provide a desired optical effect, such as reducing an aberration of the ophthalmic lens 300 or the eye.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An ophthalmic lens, comprising:
   an optic having an anterior surface, a posterior surface, and an optical axis, the optic comprising;
      a first region having a first refractive optical power and comprising a first base curvature having a finite first radius of curvature and a first phase plate having at least one diffraction order with a diffractive optical power, the first region configured for forming a first focus and a second focus; and
      a second region having a second refractive optical power and comprising a second base curvature having a finite second radius of curvature that is different from the first radius of curvature and a second phase plate having at least one diffraction order with a diffractive optical power, the second region configured for forming a third focus that is between the first focus and the second focus.

2. The ophthalmic lens of claim 1, wherein the first focus is configured to provide distant vision, the second focus is configured to provide near vision, and the third focus is configured to provide intermediate vision.

3. The ophthalmic lens of claim 1, wherein the second phase plate is a monofocal phase plate.

4. The ophthalmic lens of claim 1, wherein the second phase plate is a multifocal phase plate.

5. The ophthalmic lens of claim 1, wherein the second region is disposed about the first region.

6. The ophthalmic lens of claim 1, wherein light at a design wavelength that is incident on the ophthalmic lens is split between a zeroth diffraction order and a first diffraction order, the zeroth diffraction order having no optical power.

7. The ophthalmic lens of claim 1, wherein light at a design wavelength that is incident on the ophthalmic lens is split between a first order and second diffraction order.

8. The ophthalmic lens of claim 1, wherein the first region comprises a first plurality of echelettes having a first step height between adjacent echelettes and the second region comprise a second plurality of echelettes having a second step height between adjacent echelettes, the second step height being less than the first step height.

9. The ophthalmic lens of claim 1, wherein the ophthalmic lens is an intraocular lens comprising one or more haptics.

10. The ophthalmic lens of claim 9, wherein the one or more haptics is made of the same material as the optic.

11. The ophthalmic lens of claim 9, wherein the one or more haptics is integrally formed with the optic to form a one-piece intraocular lens.

* * * * *